United States Patent
Wipf et al.

(10) Patent No.: US 10,882,834 B2
(45) Date of Patent: *Jan. 5, 2021

(54) COMPOUNDS FOR TREATING PROSTATE CANCER

(71) Applicant: University of Pittsburgh—of the Commonwealth System of Higher Education, Pittsburgh, PA (US)

(72) Inventors: Peter Wipf, Pittsburgh, PA (US); Erin M. Skoda, Columbia, MD (US); Zhou Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,349

(22) PCT Filed: Sep. 18, 2014

(86) PCT No.: PCT/US2014/056369
§ 371 (c)(1),
(2) Date: Mar. 18, 2016

(87) PCT Pub. No.: WO2015/042297
PCT Pub. Date: Mar. 26, 2015

(65) Prior Publication Data
US 2016/0264540 A1    Sep. 15, 2016

Related U.S. Application Data

(60) Provisional application No. 61/880,747, filed on Sep. 20, 2013.

(51) Int. Cl.
| | | |
|---|---|---|
| *A61K 31/495* | (2006.01) | |
| *C07D 295/185* | (2006.01) | |
| *C07D 295/192* | (2006.01) | |
| *A61K 45/06* | (2006.01) | |
| *C07D 295/26* | (2006.01) | |
| *C07D 213/70* | (2006.01) | |

(Continued)

(52) U.S. Cl.
CPC ...... *C07D 295/192* (2013.01); *A61K 31/4525* (2013.01); *A61K 31/495* (2013.01); *A61K 31/496* (2013.01); *A61K 31/551* (2013.01); *A61K 31/58* (2013.01); *A61K 45/06* (2013.01); *C07D 213/70* (2013.01); *C07D 261/08* (2013.01); *C07D 295/26* (2013.01); *C07D 317/54* (2013.01); *C07D 333/16* (2013.01); *C07D 413/12* (2013.01)

(58) Field of Classification Search
CPC ............. C07D 295/192; C07D 317/54; C07D 333/16; C07D 413/12; C07D 295/26; C07D 261/08; C07D 213/70; A61K 45/06; A61K 31/4525; A61K 31/58; A61K 31/496; A61K 31/551; A61K 31/495
See application file for complete search history.

(56) References Cited

U.S. PATENT DOCUMENTS

| 4,186,205 A | 1/1980 | Bender |
| 5,292,758 A | 3/1994 | Yoshino et al. |

(Continued)

FOREIGN PATENT DOCUMENTS

| EP | 1 340 749 | 9/2003 |
| EP | 1 437 349 | 7/2004 |

(Continued)

OTHER PUBLICATIONS

Anne Valade, Sophie Binet Cross, Claire Brown, Eric Detrait, Doina Ene, Michel Gillard, Michel Guyaux, Yves Lamberty, Martin Maguire, Nivedita Namdev, Laurent Provins, Eric Schwartz, and Celine Vermeirena, Discovery of novel selective Sigma-1 ligands as cognitive enhancers, Med. Chem. Commun., 201.*

(Continued)

*Primary Examiner* — Sarah Pihonak
*Assistant Examiner* — Jason Deck
(74) *Attorney, Agent, or Firm* — Klarquist Sparkman, LLP

(57) ABSTRACT

A compound, or a pharmaceutically acceptable salt or ester thereof, having a formula I of: $R^{20}$—$(Z)_b$—$(Y)_c$—$(R^{21})_a$—X—$R^{22}$—$R^{23}$ wherein R20 is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group; Z is alkanediyl, substituted alkanediyl, cycloalkanediyl, or substituted cycloalkanediyl; Y is S, O, or $NR^{10}$, wherein $R^{10}$ is H or alkyl; $R^{21}$ is alkanediyl, substituted alkanediyl, cycloalkanediyl, substituted cycloalkanediyl, alkadienyl, substituted alkadienyl, alkatrienyl, substituted alkatrienyl; X is —C(=O)- or —S(=O)(=O)-; $R^{22}$ is a moiety that includes at least one divalent amino radical; $R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group; a is 0 or 1; b is 0 or 1; and c is 0 or 1; provided that if X is —C(=O)- then Y is not S.

15 Claims, 10 Drawing Sheets

(51) Int. Cl.
  *C07D 333/16* (2006.01)
  *C07D 261/08* (2006.01)
  *C07D 317/54* (2006.01)
  *C07D 413/12* (2006.01)
  *A61K 31/4525* (2006.01)
  *A61K 31/551* (2006.01)
  *A61K 31/58* (2006.01)
  *A61K 31/496* (2006.01)

(56) References Cited

U.S. PATENT DOCUMENTS

| | | |
|---|---|---|
| 5,317,019 A | 5/1994 | Bender et al. |
| 5,929,097 A | 7/1999 | Levin et al. |
| 6,586,617 B1 | 7/2003 | Tabuchi et al. |
| 6,680,342 B2 | 1/2004 | Young et al. |
| 6,723,730 B2 | 4/2004 | Bakthavatchalam et al. |
| 2002/0022630 A1 | 2/2002 | Zhang et al. |
| 2004/0092529 A1 | 5/2004 | Blumberg et al. |
| 2007/0142394 A1 | 6/2007 | Solomon et al. |
| 2009/0163545 A1 | 6/2009 | Goldfarb |
| 2010/0094006 A1 | 4/2010 | Nam et al. |
| 2011/0003839 A1 | 1/2011 | Jung et al. |
| 2012/0264744 A1 | 10/2012 | Dasgupta et al. |
| 2013/0211075 A1 | 8/2013 | Ushio et al. |
| 2014/0371235 A1 | 12/2014 | Wang et al. |

FOREIGN PATENT DOCUMENTS

| | | |
|---|---|---|
| EP | 1992618 | 11/2008 |
| JP | 2001 261657 | 9/2001 |
| WO | WO 99/02502 | 1/1999 |
| WO | WO 00/40572 | 7/2000 |
| WO | WO 00/54759 | 9/2000 |
| WO | WO 2001/029038 | 4/2001 |
| WO | WO 02/30879 | 4/2002 |
| WO | WO 2004/014300 | 2/2004 |
| WO | WO 2004/073634 | 9/2004 |
| WO | WO 2005/040114 | 5/2005 |
| WO | WO 2005/079270 | 9/2005 |
| WO | WO 2005/121130 | 12/2005 |
| WO | WO 2006/030977 | 3/2006 |
| WO | WO 2006/044504 | 4/2006 |
| WO | WO 2007/002701 | 1/2007 |
| WO | WO 2007/061360 | 5/2007 |
| WO | WO 2007/071440 | 6/2007 |
| WO | WO 2007/071443 | 6/2007 |
| WO | WO 2007/076055 | 7/2007 |
| WO | WO 2008/011130 | 1/2008 |
| WO | WO 2008/027584 | 3/2008 |
| WO | WO 2008/060998 | 5/2008 |
| WO | WO 2008/114022 | 9/2008 |
| WO | WO 2009/092585 | 7/2009 |
| WO | WO 2009/125923 | 10/2009 |
| WO | WO 2011/032169 | 3/2011 |
| WO | WO 2011/050353 | 4/2011 |
| WO | WO 2013/055793 | 4/2013 |
| WO | WO 2013/117963 | 8/2013 |

OTHER PUBLICATIONS

PubChem entry for SCHEMBL18061526; Entered May 29, 2009
PubChem entry for ST50917073; Entered Sep. 13, 2005 PubChem entry for ACILTCGH; Entered Jul. 11, 2005 PubChem entry for CID 24884553; Entered Sep. 8, 2008.*
Timothy J. Waybright,1 John R. Britt,2 and Thomas G. McCloud2, Overcoming Problems of Compound Storage in DMSO: Solvent and Process Alternatives, Journal of Biomolecular Screening 14(6); 2009 (Year: 2009).*
ZINC474553 (Year: 2004).*
ZINC474556 (Year: 2004).*
ZINC1480379 (Year: 2004).*
ZINC1480382 (Year: 2004).*
Ai et al., "HDAC6 Regulates Androgen Receptor Hypersensitivity and Nuclear Localization via Modulating Hsp90 Acetylation in Castration-resistant Prostate Cancer," *Mol. Endocrinol.*, 23(12): 1963-1972, 2009.
Bravo-Altamirano et al. "Synthesis and Structure-Activity Relationships of Benzothienothiazepinone Inhibitors of Protein Kinase D," *ACS Med. Chem. Lett.*, 2:154-159, 2011.
CAS RN 1172844-15-3, STN Entry Date: Aug. 5, 2009.
CAS RN 1179381-92-0, STN Entry Date: Sep. 2, 2009.
CAS RN 1179384-26-9, STN Entry Date: Sep. 2, 2009.
CAS RN 1179402-21-1, STN Entry Date: Sep. 2, 2009.
CAS RN 312929-26-3, STN Entry Date: Jan. 5, 2001.
CAS RN 321981-09-3, STN Entry Date: Feb. 19, 2001.
CAS RN 326014-86-2, STN Entry Date: Mar. 7, 2001.
CAS RN 344565-06-6, STN Entry Date: Jul. 5, 2001.
CAS RN 345293-88-1, STN Entry Date: Jul. 11, 2001.
CAS RN 475196-08-8, STN Entry Date: Dec. 5, 2002.
CAS RN 790203-53-1, STN Entry Date: Nov. 29, 2004.
CAS RN 893704-98-8, STN Entry Date: Jul. 17, 2006.
Clausen et al. "In Vitro Cytoxicity and in Vivo Efficacy, Pharmacokinetics, and Metabolism of 10074-G5, a Novel Small-MoleculeInhibitor of c-Myc/Max Dimerization," *The Journal of Pharmacology and Experimental Therapeutics*, 335(3): 715-727, 2010.
Claxton et al., "Cyclization of Lactamimide Ketones to Imidazo[1,2-a]-azacycloalkanes with Hypoglycemic Activity", *Journal of Medicinal Chemistry*, 17(3): 364-367, 1974.
Demchenko et al., "Synthesis and antimycotic activity of 3-aryl-6,7-dihydro-5H-pyrrolo[1,2-a imidazoles", *Khimiko-Farmatsevticheskii Zhurnal.*, 21(11): 1335-1338, 1987.
Frantz et al., "Large-Scale asymmetric Synthesis of the Bioprotective Agent JP4-039 and Analogs," *Organic Letters*, 2011.
Frutos et al., "Expedient synthesis of substituted imidazoles from nitriles," *Tetrahedrom Letters*, 46: 8369-8372, 2005.
Graczyk et al., "The neuroprotective action of JNK3 inhibitors based on the , 7-dihydro-5H-pyrrolo[1,2-a]imidazole scaffold," *Bioorganic & Medical Chemistry Letters*, 15: 4666-4670, 2005.
International Search Report issued for International Application No. PCT/US2014/056369, dated Jan. 14, 2015.
International Search Report issued for International Application No. PCT/US2012/059558, dated Jan. 18, 2013.
Kovtunenko et al., "Derivatives of 2a,4a-diazacyclopent[c,d]azulene", *Khimiya Geterotsiklicheskikh Soedinenii.*, 8: 1072-1077, 1996. (translated abstract only).
Kovtunenko et al., "Derivatives of 1,2-tetramethyleneimidazole", *Ukrainskii Khimicheskii Zhurna (Russian Edition)*, 62(3-4): 111-117, 1996. (translated abstract only).
Liu et al., "A general and convenient synthesis of N-aryl piperazines," *Tetrahedron Letters*, 46: 7921-7922, 2005.
O'Shaughnessy et al., "Synthesis of Pyrrolo- and Pyrido-[1,2-a]benzimidazolequinone Anti-tumor Agents Containing a Fused Cyclopropane Ring," *Synthesis*, 7: 1069-1076, 2005.
Paone et al., "Orally bioavailable imidazoazepanes as calcitonin gene-related peptide (CGRP) receptoragntagonists: Discovery of MK-2918", *Bioorganic and Medicinal Chemistry Letters*, 21:2683-2686, 2011.
Ren et al., "Pharmacophore modeling and virtual screening for the discovery of new transforming growth factor-beta type I receptor (ALK5) inhibitors", *European Journal of Medicinal Chemistry*, 44: 4259-4265, 2009.
Saporita et al., "The Hsp90 Inhibitor, 17-AAG, Prevents the Ligand-Independent Nuclear Localization of Androgen Receptor in Refractory Prostate Cancer Cells," *The Prostate*, 67: 509-520, 2007.
Sasaki et al., "Ring transformation of oxazoles to fused imidazoles. New synthetic route for 6-methyl-2,3-diphenyl-7,8-dihydroimidazo[1,2-b]pyridazine and 5-methyl-2,3-diphenyl-6,7-dihydro-5H-pyrrolo[1,2-a]imidazole, and their perhydrobenzo analogs", *Journal of the Chemical Society, Perkin Transactions 1: Organic and Bio-Organic Chemistry*, 12: 3027-3030, 1983.
U.S. Appl. No. 14/351,126, filed Apr. 10, 2014.
U.S. Appl. No. 15/080,237, filed Mar. 24, 2016.

(56) References Cited

OTHER PUBLICATIONS

Whitlock et al., "Potent and selective α$_{1A}$ adrenoceptor partial agonists—Novel imidazole frameworks," *Bioorganic & Medicinal Chemistry Letters*, 19: 3118-3121, 2009.
Written Opinion issued for International Application No. PCT/US2014/056369, dated Jan. 14, 2015.
Written Opinion issued for International Application No. PCT/US2012/059558, dated Jan. 18, 2013.
PubChem CID No. 1530082, created Jul. 11, 2005.
Extended European Search Report issued by the European Patent Office for EPC Application No. EP 14846330 dated Jun. 14, 2017.
U.S. Appl. No. 15/457,782, filed Mar. 13, 2017.
Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," *J. Org. Chem.*, vol. 68, pp. 9255-9262, 2003.
ZINC17074676 added Sep. 13, 2008.
ZINC2562103 added Oct. 27, 2004.
ZINC25951622 added Feb. 2, 2009.
ZINC25951626 added Feb. 2, 2009.
ZINC25951633 added Feb. 2, 2009.
ZINC25958726 added Feb. 2, 2009.
ZINC25958734 added Feb. 2, 2009.
ZINC30778696 added Apr. 2, 2009.
ZINC30778703 added Apr. 2, 2009.
ZINC3135710 added Nov. 6, 2004.
ZINC38946613 added Feb. 1, 2010.
ZINC38946614 added Feb. 1, 2010.
ZINC38946616 added Feb. 1, 2010.
ZINC39755011 added Mar. 7, 2010.
ZINC54116237 added Nov. 30, 2010.
ZINC54116241 added Nov. 30, 2010.
ZINC58469525 added Feb. 7, 2011.
ZINC72011928 added Feb. 23, 2012.
ZINC92210938 added Jun. 14, 2013.
ZINC92210944 added Jun. 14, 2013.
CAS RN 1624152-83-5, STN Entry Date: Sep. 22, 2014.
CAS RN 1624387-89-8, STN Entry Date: Sep. 23, 2014.
CAS RN 1646734-73-7, STN Entry Date: Feb. 12, 2015.
CAS RN 1647452-68-3, STN Entry Date: Feb. 15, 2015.
International Search Report and Written Opinion issued for International Application No. PCT/US2017/024105, dated Jun. 29, 2017.
Final Office Action issued for U.S. Appl. No. 15/080,237 dated Dec. 26, 2017.
U.S. Appl. No. 15/961,475, filed Apr. 24, 2018.
ZINC303410047 added Mar. 11, 2016.
ZINC303692363 added Mar. 11, 2016.
ZINC303878919 added Mar. 11, 2016.
Johnson et al., "Small molecule antagonists of the nuclear androgen receptor for the treatment of castration-resistant prostate cancer," *ACS Medicinal Chemistry Letters*, vol. 7, pp. 785-790, May 27, 2016.
Non-Final Office Action issued for U.S. Appl. No. 16/139,950 dated Jun. 25, 2019.
U.S. Appl. No. 16/139,950, filed Sep. 24, 2018.
Zhang et al., "trans-1-[(2-Phenylcyclopropyl)methyl]-4-arylpiperazines: Mixed Dopamine D2/D4 Receptor Antagonists as Potential Antipsychotic Agents," *J. Med. Chem.*, vol. 43, pp. 3923-3932, Sep. 30, 2000.
Examination Report issued by European Patent Office for EPC Application No. 14846330.0 dated Oct. 25, 2019.

* cited by examiner

FIG. 1A

| Compound Name | Shortened # | Structure | MW (exact) | Formula |
|---|---|---|---|---|
| PW9-09 | 909 | 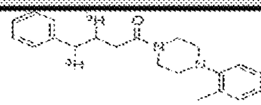 | 326.22 | C21H24T2N2O |
| MK504-92 | 492 | 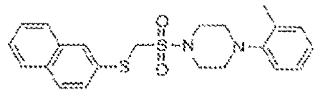 | 412.13 | C22H24N2O2S2 |
| MK504-91 | 491 | 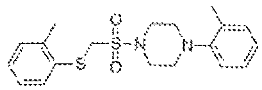 | 376.13 | C19H24N2O2S2 |
| MK504-90 | 490 | 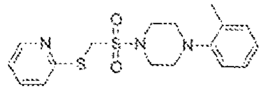 | 363.11 | C17H21N3O2S2 |
| EMS386-73 | 673 | | 320.43 | C21H24N2O |
| MK504-63 | 463 | 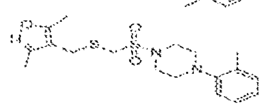 | 395.13 | C18H25N3O3S2 |
| MK504-37 | 437 | 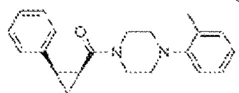 | 320.19 | C21H24N2O |
| EMS386-23 | 623 | | 412.18 | C23H28N2O3S |
| EMS386-15 | 615 | | 306.17 | C20H22N2O |
| EMS386-08 | 608 | | 308.16 | C20H20N2O |
| EMS386-07 | 607 | | 306.17 | C20H22N2O |
| BRE490-17 | 17 | 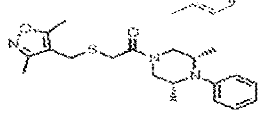 | 373.18 | C20H27N3O2S |
| BRE490-18 | 18 | 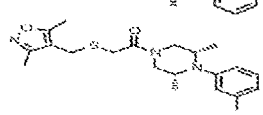 | 387.2 | C21H29N3O2S |
| BRE490-22 | 22 | 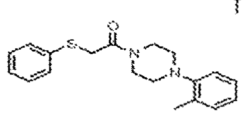 | 326.15 | C19H22N2OS |
| BRE454-84 | 484 | 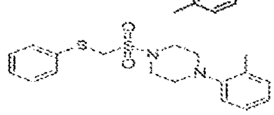 | 362.11 | C18H22N2O2S2 |
| MK415-59 | 559 | 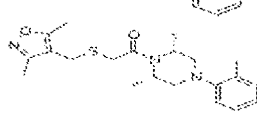 | 387.54 | C21H29N3O2S |
| MK415-62 | 562 | 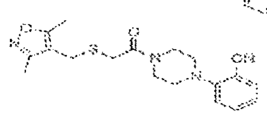 | 370.47 | C19H22N4O2S |

FIG. 1B

| ID | No. | Structure | MW | Formula |
|---|---|---|---|---|
| MK415-63 | 563 | 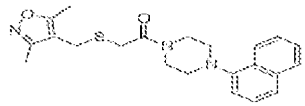 | 395.52 | C22H25N3O2S |
| MK415-48 | 548 | 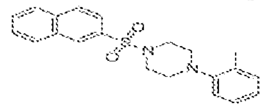 | 366.48 | C21H22N2O2S |
| MK415-53 | 553 | 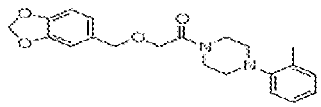 | 368.43 | C21H24N2O4 |
| MK415-47 | 547 | 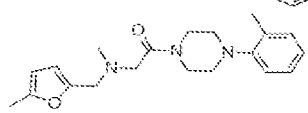 | 341.45 | C20H27N3O2 |
| BRE454-62 | 462 | 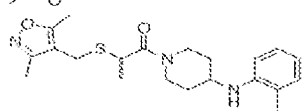 | 387.54 | C21H29N3O2S |
| BRE454-75 | 475 | 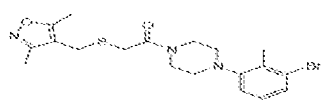 | 438.38 | C19H24BrN3O2S |
| BRE454-76 | 476 | 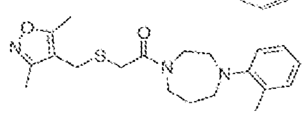 | 373.41 | C20H27N3O2S |
| BRE454-71 | 471 | 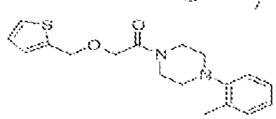 | 330.14 | C18H22N2O2S |
| BRE454-78 | 478 | 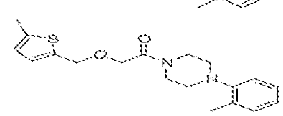 | 344.16 | C19H24N2O2S |
| BRE454-58 | 458 | 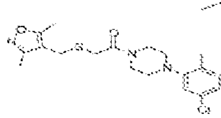 | 393.93 | C19H24ClN3O2S |
| BRE454-56 | 456 | 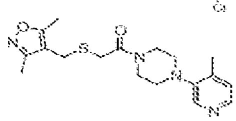 | 360.47 | C18H24N4O2S |
| BRE454-46 | 446 | 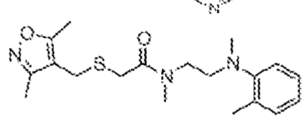 | 361.5 | C19H27N3O2S |
| MK415-43-2 | 543 | 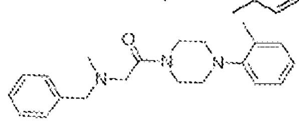 | 337.46 | C21H27N3O |
| BRE454-43 | 443 | 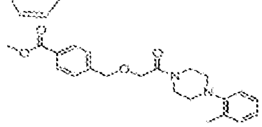 | 382.45 | C22H26N2O4 |
| BRE454-54 | 454 | 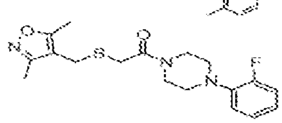 | 363.45 | C18H22FN3O2S |
| BRE454-47 | 447 | 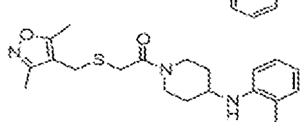 | 373.51 | C20H27N3O2S |

COMPOUNDS FOR TREATING PROSTATE CANCER

This application is the U.S. National Stage of International Application No. PCT/US2014/056369, filed Sep. 18, 2014, which was published in English under PCT Article 21(2), which in turn claims the benefit of U.S. provisional application 61/880,747, filed Sep. 20, 2013, which is incorporated herein by reference.

ACKNOWLEDGMENT OF GOVERNMENT SUPPORT

This invention was made with government support under grant # GM067082 awarded by the National Institutes of Health. The government has certain rights in the invention.

BACKGROUND

Castration-resistant prostate cancer (CRPC) is currently incurable and makes prostate cancer the second most common cause of cancer death among men in the United States. Multiple studies have shown that the androgen receptor (AR) is activated via multiple mechanisms including AR overexpression, mutation, hypersensitization, and/or intratumoral androgen synthesis in patients relapsed after androgen deprivation therapy (ADT). Overexpression and knockdown studies have demonstrated that AR is a key molecular determinant and an excellent therapeutic target for CRPC. Abiraterone, a potent inhibitor of testosterone synthesis, and MDV3100, a novel AR antagonist, are still effective in the treatment of CRPC, indicating that AR remains a viable target in the majority of CRPC patients.

Androgen receptor (AR), a member of the steroid receptor superfamily, is a ligand-dependent transcription factor that controls the expression of androgen-responsive genes. Intracellular trafficking is an important mechanism in the regulation of many transcription factors, including AR. In order to access its target genes, a transcription factor requires localization to the nucleus. Retention of a transcription factor in the cytoplasm prevents its activity. Thus, a key regulatory step in the action of AR is its nuclear translocation. In androgen-sensitive cells, AR is localized to the cytoplasm in the absence of ligand. Upon addition of androgens, AR translocates to the nucleus and transactivates target genes. However, in CRPC cells, AR remains in the nucleus even in the absence of androgen and transactivates androgen-responsive genes, leading to uncontrolled growth of prostate tumors. Therefore, novel approaches that can block the nuclear localization of AR may provide an effective therapy against CRPC.

SUMMARY

Disclosed herein is a compound, or a pharmaceutically acceptable salt or ester thereof, having a formula I of:

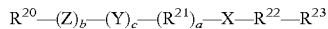

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;
Z is alkanediyl, substituted alkanediyl, cycloalkanediyl, or substituted cycloalkanediyl;
Y is S, O, or $NR^{10}$, wherein $R^{10}$ is H or alkyl;
$R^{21}$ is alkanediyl, substituted alkanediyl, cycloalkanediyl, substituted cycloalkanediyl alkadienyl, substituted alkadienyl, alkatrienyl, substituted alkatrienyl;
X is —C(=O)— or —S(=O)(=O)—;
$R^{22}$ is a moiety that includes at least one divalent amino radical;
$R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;
a is 0 or 1;
b is 0 or 1; and
c is 0 or 1;
provided that if X is —C(=O)— then Y is not S.

Further disclosed herein is a compound, or a pharmaceutically acceptable salt or ester thereof, having a formula II of:

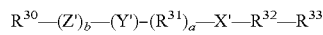

wherein $R^{30}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;
Z' is alkanediyl, or substituted alkanediyl;
Y' is S;
$R^{31}$ is alkanediyl or substituted alkanediyl;
X is —C(=O)—;
$R^{32}$ is a moiety that includes at least one divalent amino radical;
$R^{33}$ is a phenyl substituted with at least one halogen or cyano;
a is 0 or 1; and
b is 0 or 1.

Also disclosed herein is a method for treating prostate cancer in a subject, comprising administering a therapeutically effective amount of an agent to the subject, wherein the agent is a compound, or a pharmaceutically acceptable salt or ester thereof, of formula I.

Additionally disclosed herein is a method for treating prostate cancer in a subject, comprising administering a therapeutically effective amount of an agent to the subject, wherein the agent is a compound, or a pharmaceutically acceptable salt or ester thereof, of formula II.

The foregoing will become more apparent from the following detailed description, which proceeds with reference to the accompanying figures.

BRIEF DESCRIPTION OF THE DRAWINGS

FIGS. 1A and 1B is a table showing compound structures.

DETAILED DESCRIPTION

Figure 2A:
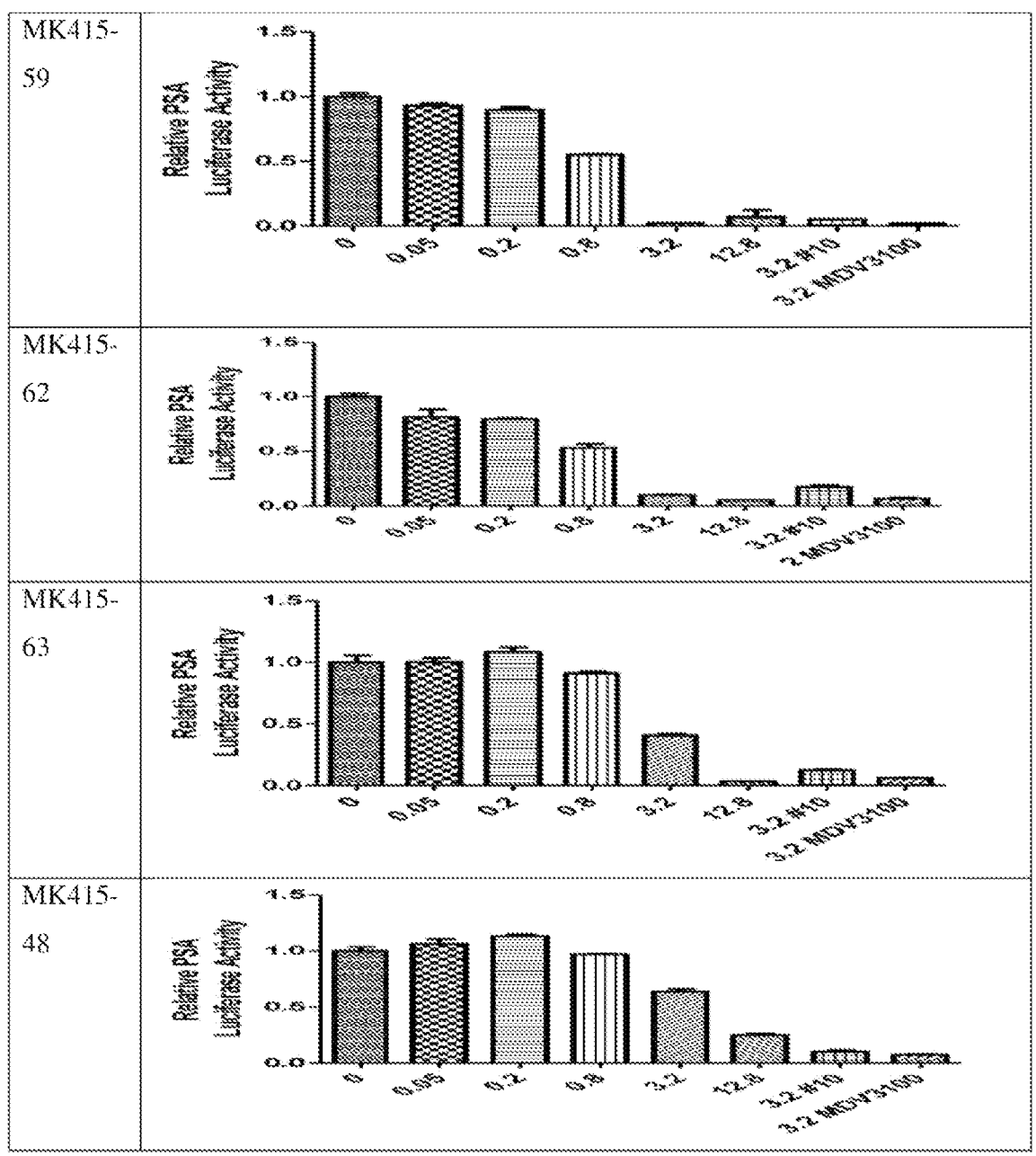
FIG. 2A through 2E shows assay results for several of the compounds. C4-2 cells were transfected with PSA6.1-Luc, GFP-AR, and pRL-CMV and then treated with indicated doses for 24 hours. For luciferase assays, cells were lysed with passive lysis buffer (Promega) and both Firefly and Renilla luciferase activities were read using a Dual-Luciferase Reporter Assay kit (Promega) on a LmaxII384 luminometer (Molecular Devices). Firefly luciferase values were normalized to Renilla (pRL-CMV) Plotted values represent averaged normalized Firefly luciferase activities, each performed in triplicate, relative to DMSO control. This assay is described in more detail in PCT Patent Application Publication WO 2013055793, which is incorporated herein by reference.
Figure 2B:
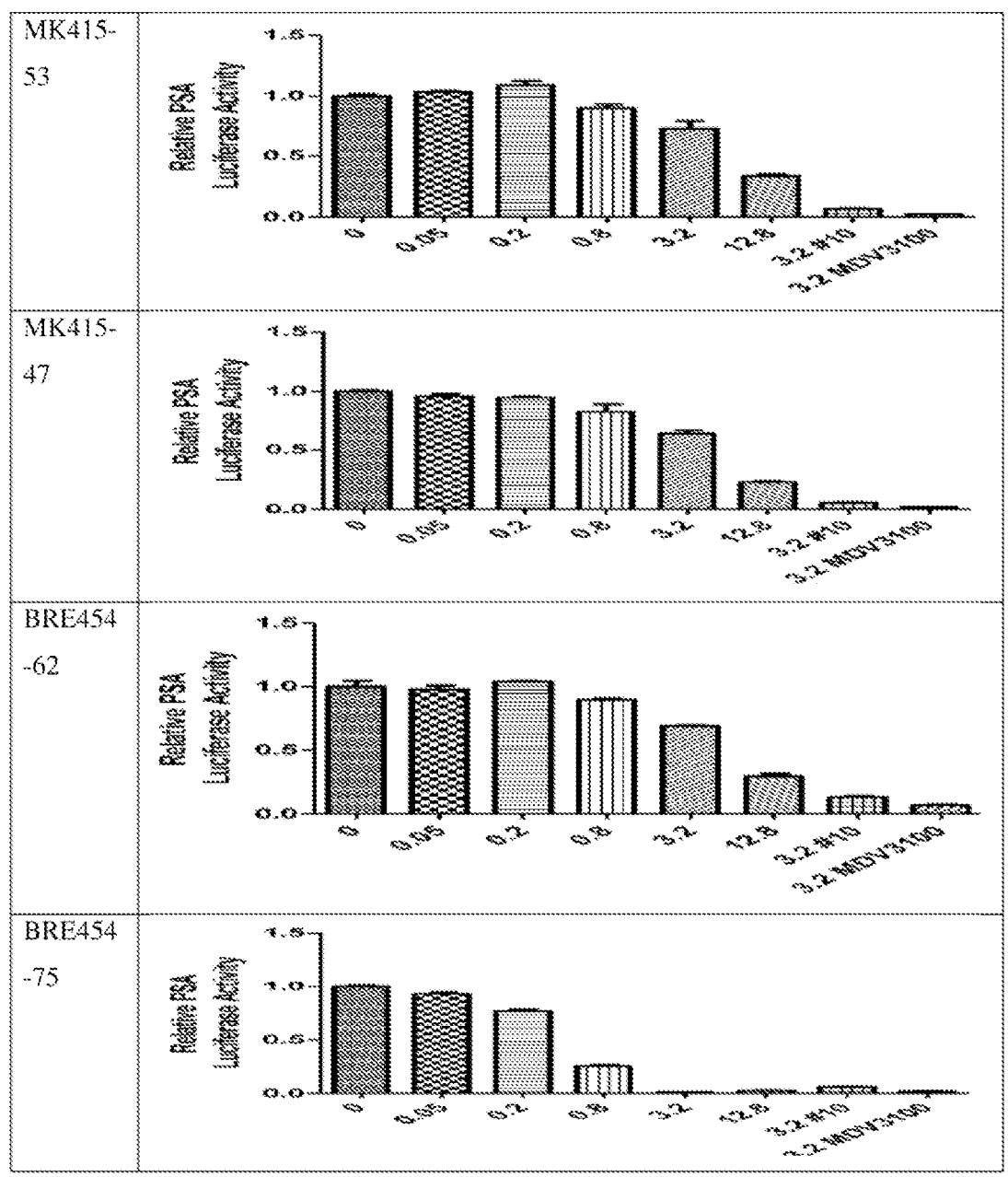
Figure 2C:
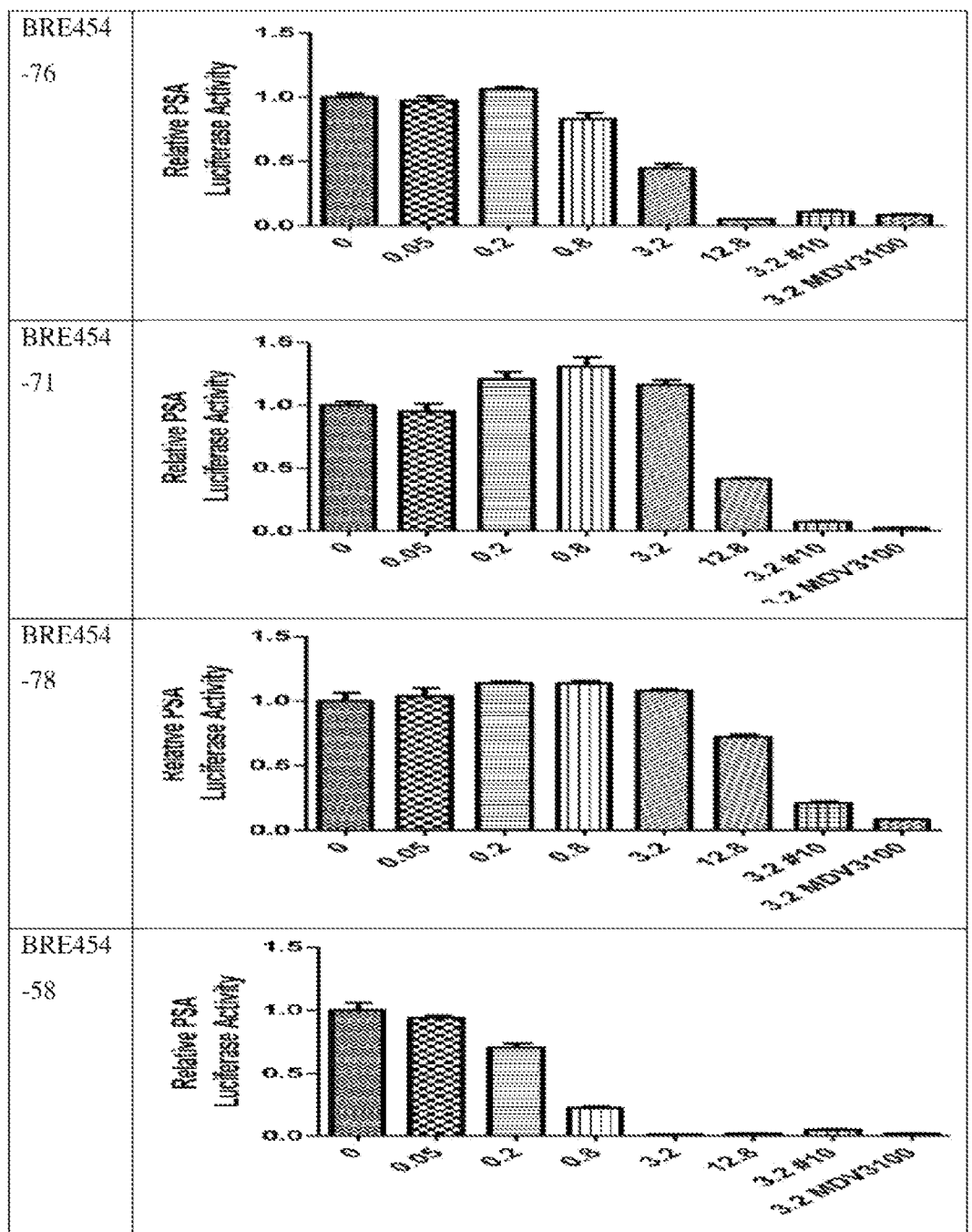
Figure 2D:
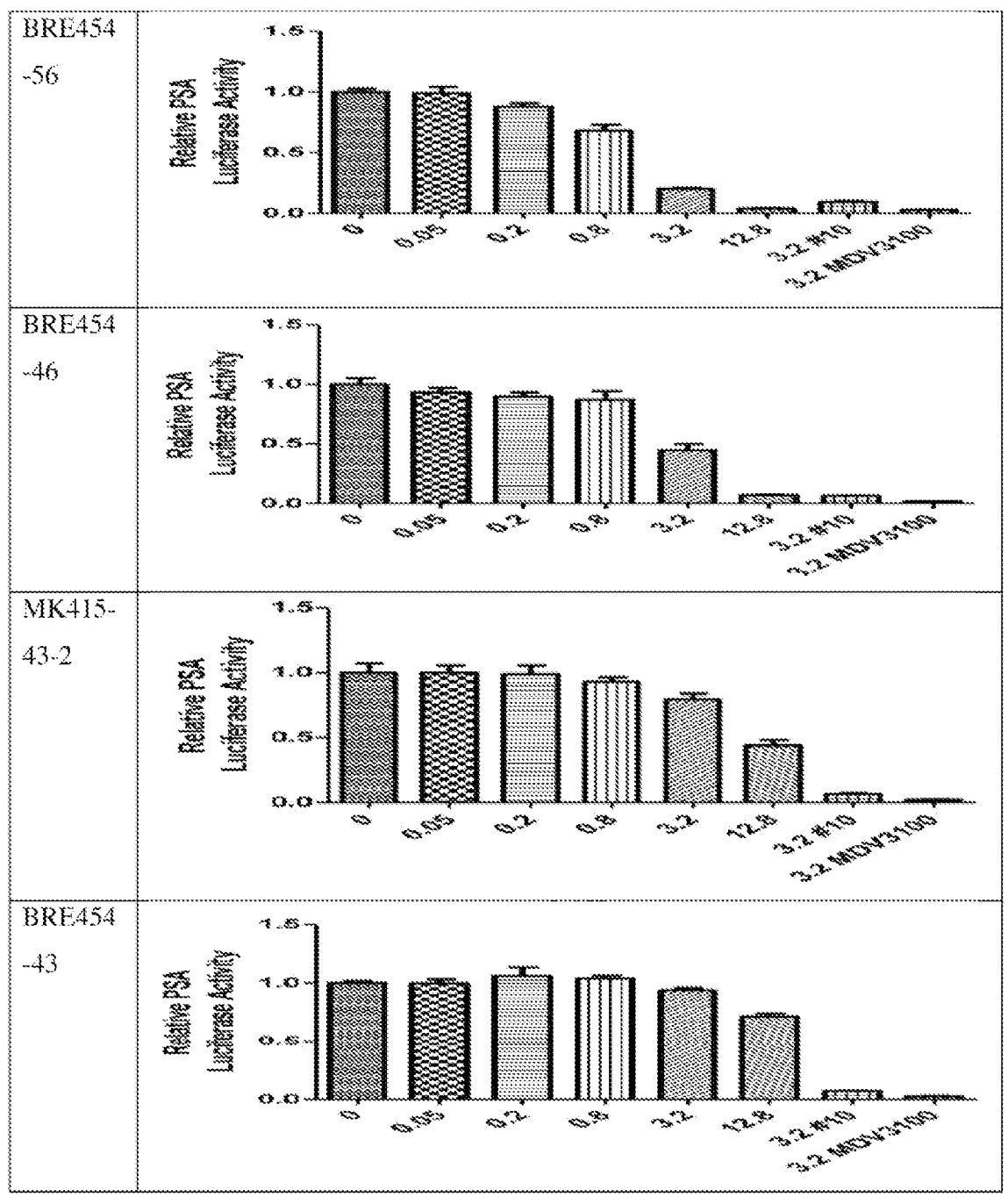
Figure 2E:
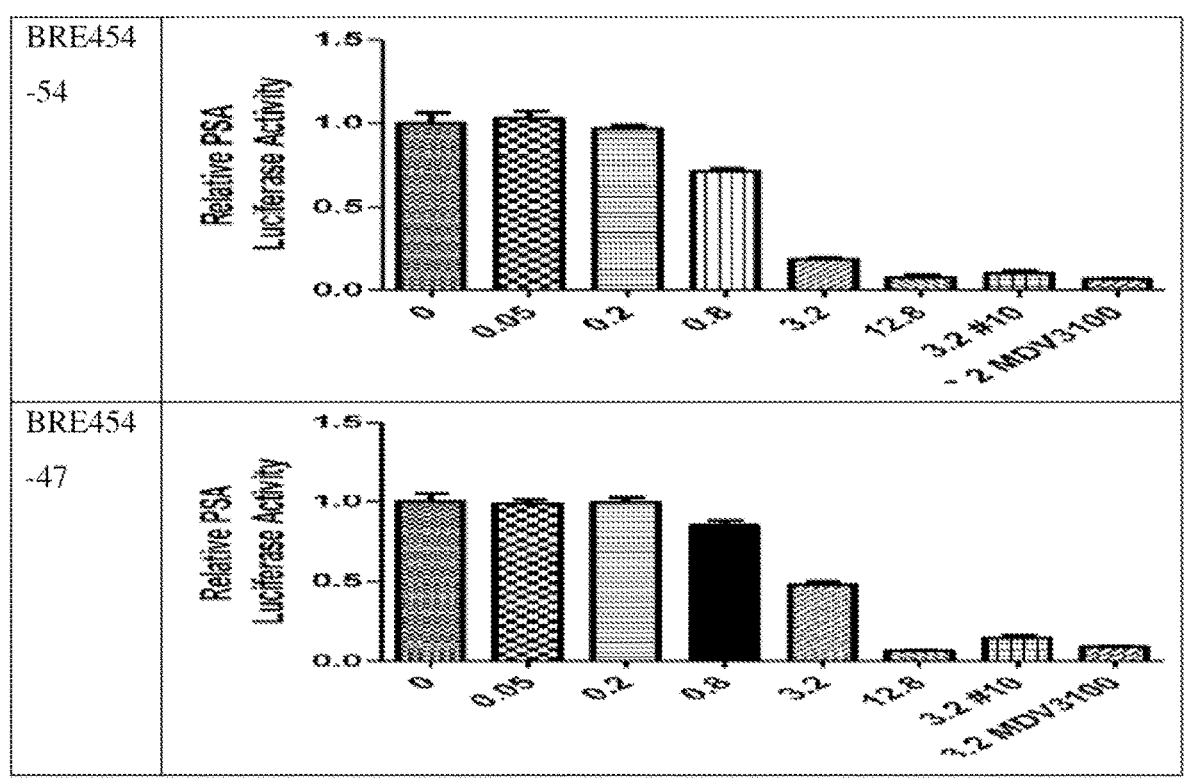

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Alkanediyl" or "cycloalkanediyl" refers to a divalent radical of the general formula —$C_nH_{2n}$— derived from aliphatic or cycloaliphatic hydrocarbons.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amide" or "amido" is represented by the formula —C(O)NRR', where R and R' independently can be a hydrogen, alkyl, alkenyl, alkynyl, aryl, arylalkyl, cycloalkyl, halogenated alkyl, or heterocycloalkyl group described above. A suitable amido group is acetamido.

The term "amine" or "amino" refers to a group of the formula —NRR', where R and R' can be, independently, hydrogen or an alkyl, alkenyl, alkynyl, aryl, arylalkyl, carbonyl (e.g, —C(O)R", where R" can be hydrogen, an alkyl, alkenyl, alkynyl, aryl, or an arylalkyl), cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, arylalkyl, cycloalkyl, cycloalkylalkyl, alkanoyl, alkoxycarbonyl, aralkoxycarbonyl and the like. An aminocarbonyl group may be —C(O)—N(R) (wherein R is a substituted group or H). An "aminocarbonyl" is inclusive of an amido group. A suitable aminocarbonyl group is acetamido.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "arylalkyl" refers to an alkyl group where at least one hydrogen atom is substituted by an aryl group. An example of an arylalkyl group is a benzyl group.

"Carbonyl" refers to a group of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COO group. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "co-administration" or "co-administering" refers to administration of a first agent with a second agent within the same general time period, and does not require administration at the same exact moment in time (although co-administration is inclusive of administering at the same exact moment in time). Thus, co-administration may be on the same day or on different days, or in the same week or in different weeks. The first agent and the second agent may be included in the same composition or they may each individually be included in separate compositions. In certain embodiments, the two agents may be administered during a time frame wherein their respective periods of biological activity overlap. Thus, the term includes sequential as well as coextensive administration of two or more agents.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen hetero atom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$ alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$ alkyl)amino. Unless otherwise defined optionally substituted N-heterocyclics includes pyridinium salts and the N-oxide form of suitable ring nitrogens.

Examples of N-heterocycles also include bridged groups such as, for example, azabicyclo (for example, azabicyclooctane).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), arylalkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or arylalkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

The term "subject" includes both human and veterinary subjects.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

CRPC is responsible for all prostate cancer deaths, and eventually all prostate cancer will develop into CRPC. The current best treatment for CRPC is MDV3100, which binds to androgen receptor. It is effective against a number of androgen-dependent prostate cancer cell lines. However, it is ineffective against the androgen-dependent prostate cancer cell line 22Rv1. Compounds disclosed herein are effective against all androgen-dependent cell lines tested including 22Rv1, a promising and unique property.

Several of the compounds show sub-micromolar inhibition of PSA-luciferase expression in C4-2 cells. Further, cell proliferation in androgen-dependent cell lines is significantly decreased while proliferation in androgen-independent cell lines is unaffected.

Agents

Disclosed herein are agents that can be used for treating prostate cancer, particularly castration-resistant prostate cancer. The agents may inhibit AR nuclear localization and/or reduce AR levels in castration-resistant prostate cancer.

In one embodiment, the agent is a compound, or a pharmaceutically acceptable salt or ester thereof, having a formula I of:

$$R^{20}—(Z)_b—(Y)_c—(R^{21})_a—X—R^{22}—R^{23}$$

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

Z is alkanediyl, substituted alkanediyl, cycloalkanediyl, or substituted cycloalkanediyl;

Y is S, O, or $NR^{10}$, wherein $R^{10}$ is H or alkyl (preferably methyl);

$R^{21}$ is alkanediyl, substituted alkanediyl, cycloalkanediyl, substituted cycloalkanediyl, alkadienyl, substituted alkadienyl, alkatrienyl, or substituted alkatrienyl;

X is —C(=O)— or —S(=O)(=O)—;

$R^{22}$ is a moiety that includes at least one divalent amino radical;

$R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

a is 0 or 1;
b is 0 or 1; and
c is 0 or 1;
provided that if X is —C(=O)— then Y is not S.

In certain embodiments, $R^{20}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, $R^{20}$ is substituted isoxazolyl, particularly dialkyl (e.g., dimethyl)-substituted isooxazolyl, or phenyl.

In certain embodiments, $R^{21}$ is selected from $C_1$-$C_3$ alkanediyl or substituted $C_1$-$C_3$ alkanediyl (e.g., alkyl-substituted such as methyl or dimethyl), preferably $C_1$ alkanediyl (—CH$_2$—), or cycloalkanediyl, preferably cyclopropanediyl. In certain embodiments, $R^{21}$ is:

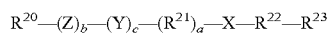

In certain embodiments, $R^{22}$ is selected from:

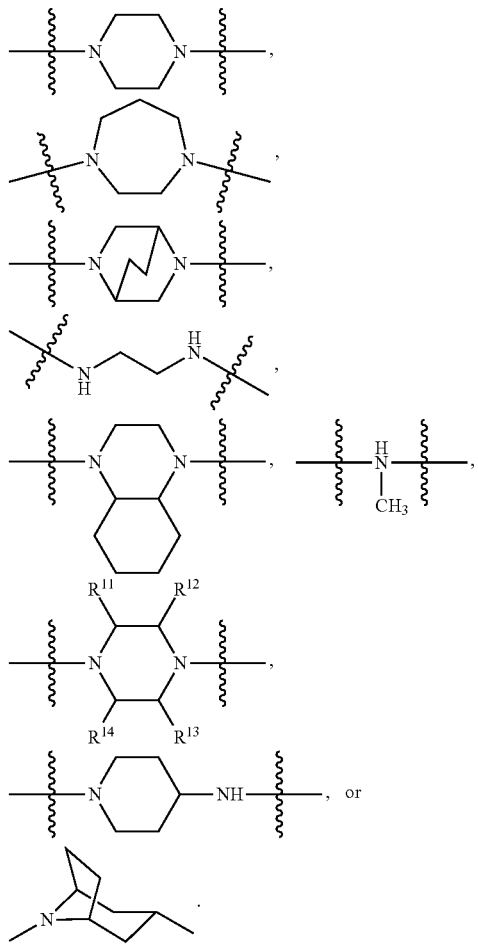

wherein $R^{11}$ to $R^{14}$ are each individually H or alkyl, provided that at least one of $R^{11}$ to $R^{14}$ is alkyl. In certain embodiments, $R^{12}$ and $R^{13}$ are each alkyl (e.g., methyl) and $R^{11}$ and $R^{14}$ are each H. In certain embodiments, $R^{11}$ and $R^{14}$ are each alkyl (e.g., methyl) and $R^{12}$ and $R^{13}$ are each H.

In certain embodiments, $R^{22}$ is a divalent radical of a N-heterocyclic group. Illustrative N-heterocylic groups include piperazinyl, substituted piperazinyl, azabicyclo (for example, azabicyclooctane), and substituted azabicyclo.

In certain embodiments, $R^{23}$ is selected from phenyl, substituted phenyl (e.g., alkyl-substituted phenyl such as dimethyl-substituted, or amino-substituted, or aminoalkyl-substituted; alkynyl-substituted phenyl), piperidinyl, substituted piperidinyl (e.g., amino-substituted), furanyl, substituted furanyl (e.g., aminoalkyl-substituted or amino-substituted), pyridinyl, substituted pyridinyl (e.g., aminoalkyl-substituted or amino-substituted), pyrimidinyl, substituted pyrimidinyl (e.g., aminoalkyl-substituted or amino-substituted), naphthenyl, substituted naphthenyl, (e.g., aminoalkyl-substituted or amino-substituted), thiazole, substituted thiazole (e.g., aminoalkyl-substituted or amino-substituted); isoindazolyl, substituted isoindazolyl (e.g., aminoalkyl-substituted or amino-substituted); triazolyl, or substituted triazolyl (e.g., aminoalkyl-substituted or amino-substituted). Preferably, $R^{23}$ is a substituted phenyl having a structure of:

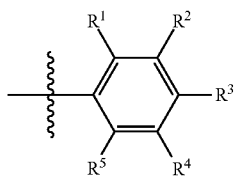

wherein each of $R^1$-$R^5$ is individually H, alkyl, substituted alkyl, alkynyl, substituted alkynyl, halogen, or cyano, provided that at least one of $R^1$-$R^5$ is not H. In certain embodiments, at least one of $R^1$-$R^5$ is halogen or cyano. In certain embodiments, $R^1$ is alkyl, halogen or cyano. In certain embodiments, at least one of $R^1$-$R^5$ is hydroxy-substituted alkynyl.

In certain embodiments, Z is selected from $C_1$-$C_3$ alkanediyl, preferably —$CH_2$—.

In certain embodiments, $R^{20}$ is phenyl or substituted isoxazolyl, b is 0; c is 1; a is 1; $R^{21}$ is —$CH_2$—, Y is S; X is —S(=O)(=O)—, $R^{22}$ is:

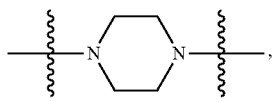 [SMILES: *N1CCN(*)CC1]

and $R^{23}$ is substituted phenyl.

In certain embodiments, $R^{21}$ is —$CH_2$—, Y is S; and X is —S(=O)(=O)—.

In certain embodiments, $R^{22}$ is:

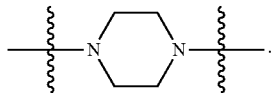

In certain embodiments, b is 0; c is 0; a is 1; and X is —C(=O)—.

In certain embodiments, b is 0; c is 0; a is 1; X is —C(=O)—; and $R^{21}$ is alkanediyl (particularly —$CH_2CH_2$—) or

In certain embodiments, b is 0; c is 0; a is 1; X is —C(=O)—; $R^{21}$ is alkanediyl (particularly —$CH_2CH_2$—) or

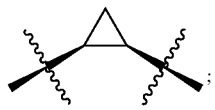 [SMILES: *[C@@H]1C[C@@H]1*]

and $R^{22}$ is

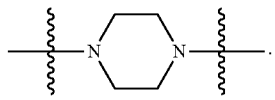 [SMILES: *N1CCN(*)CC1]

In certain embodiments, b is 0; c is 0; a is 1; X is —C(=O)—; $R^{21}$ is alkanediyl (particularly —$CH_2CH_2$—) or

$R^{22}$ is

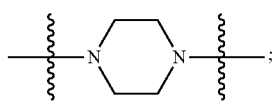

$R^{20}$ is phenyl or substituted isoxazolyl; and $R^{23}$ is substituted phenyl.

In a further embodiment, the agent is a compound, or a pharmaceutically acceptable salt or ester thereof, having a formula II of:

$$R^{30}-(Z')_b-(Y')-(R^{31})_a-X'-R^{32}-R^{33}$$

wherein $R^{30}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

Z' is alkanediyl, or substituted alkanediyl;

Y' is S;

$R^{31}$ is alkanediyl or substituted alkanediyl;

X is —C(=O)—;

$R^{32}$ is a moiety that includes at least one divalent amino radical;

$R^{33}$ is a phenyl substituted with at least one halogen or cyano;

a is 0 or 1; and b is 0 or 1.

In certain embodiments, $R^{30}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, $R^{30}$ is substituted isoxazolyl, particularly dialkyl (e.g., dimethyl)-substituted isooxazolyl, or phenyl.

In certain embodiments, Z' is selected from $C_1$-$C_3$ alkanediyl, preferably —$CH_2$—.

In certain embodiments, $R^{31}$ is selected from $C_1$-$C_3$ alkanediyl or substituted $C_1$-$C_3$ alkanediyl (e.g., alkyl-substituted such as methyl or dimethyl), preferably $C_1$ alkanediyl.

In certain embodiments, $R^{32}$ is selected from:

[chemical structures]

Preferably, $R^{33}$ is a substituted phenyl having a structure of:

[chemical structure with $R^1$, $R^2$, $R^3$, $R^4$, $R^5$]

wherein each of $R^1$-$R^5$ is individually H, alkyl, halogen, or cyano, provided that at least one of $R^1$-$R^5$ is halogen or cyano. In certain embodiments, $R^1$ is alkyl, halogen or cyano.

In certain embodiments, $R^{30}$ is substituted isoxazolyl, b is 1; a is 1; $R^{21}$ is —$CH_2$—; and $R^{32}$ is:

[chemical structure — piperazine]

Certain embodiments are described below in the following numbered clauses:

1. A compound, or a pharmaceutically acceptable salt or ester thereof, having a formula I of:

$$R^{20}-(Z)_b-(Y)_c-(R^{21})_a-X-R^{22}-R^{23}$$

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

Z is alkanediyl, or substituted alkanediyl;

Y is S, O, or $NR^{10}$, wherein $R^{10}$ is H or alkyl;

$R^{21}$ is alkanediyl, substituted alkanediyl, alkadienyl, substituted alkadienyl, alkatrienyl, substituted alkatrienyl;

X is —C(=O)— or —S(=O)(=O)—;

$R^{22}$ is a moiety that includes at least one divalent amino radical;

$R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

a is 0 or 1;

b is 0 or 1; and c is 0 or 1;

provided that if X is —C(=O)— then Y is not S.

2. The compound of clause 1, wherein $R^{20}$ is selected from isoxazolyl, substituted isoxazolyl, oxazolyl, substituted oxazolyl, cyclohexyl, substituted cyclohexyl, piperidinyl, substituted piperidinyl, oxacyclopentyl, substituted oxacyclopentyl, oxacyclohexanyl, substituted oxacyclopentyl, thiophenyl, substituted thiophenyl, phenyl, substituted phenyl, pyridinyl, substituted pyridinyl, indolyl, substituted indolyl, furanyl, substituted furanyl, imidazolyl, or substituted imidazolyl.

3. The compound of clause 2, wherein $R^{20}$ is substituted isooxazolyl or phenyl.

4. The compound of any one of clauses 1 to 3, wherein $R^{21}$ is selected from $C_1$-$C_3$ alkanediyl or substituted $C_1$-$C_3$ alkanediyl.

5. The compound of any one of clauses 1 to 4, wherein $R^{22}$ is selected from:

[chemical structures]

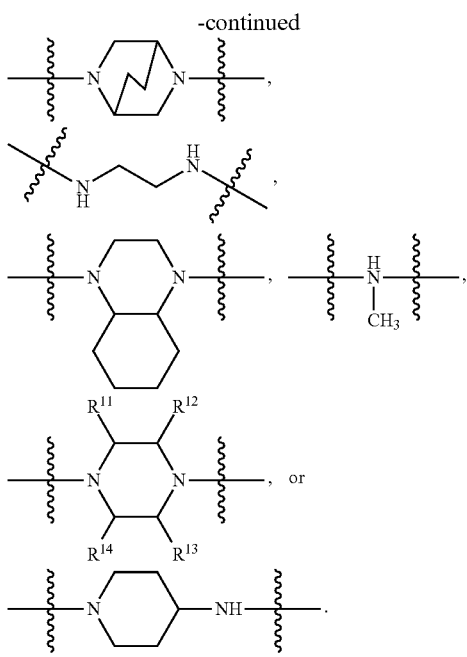

6. The compound of any one of clauses 1 to 5, wherein R²³ is selected from phenyl, substituted phenyl, piperidinyl, substituted piperidinyl, furanyl, substituted furanyl, pyridinyl, substituted pyridinyl, pyrimidinyl, substituted pyrimidinyl, naphthenyl, substituted naphthenyl, thiazole, substituted thiazole, isoindazolyl, substituted isoindazolyl, triazolyl, or substituted triazolyl.

7. The compound of any one of clauses 1 to 5, wherein R²³ is a substituted phenyl having a structure of:

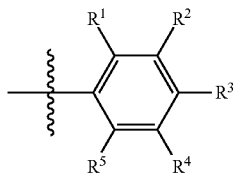

wherein each of R¹-R⁵ is individually H, alkyl, halogen, or cyano, provided that at least one of R¹-R⁵ is not H.

8. The compound of any one of clauses 1 to 7, wherein Z is selected from $C_1$-$C_3$ alkanediyl.

9. The compound of clause 1, wherein R²⁰ is phenyl or substituted isoxazolyl, b is 0; c is 1; a is 1; R²¹ is —CH₂—, Y is S; X is —S(=O)(=O)—, R²² is:

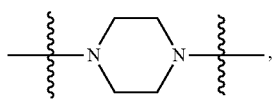

and R²³ is substituted phenyl.

10. The compound of clause 1, wherein R²¹ is —CH₂—, Y is S; and X is —S(=O)(=O)—.

11. A compound, or a pharmaceutically acceptable salt or ester thereof, having a formula II of:

R³⁰—(Z')$_b$—(Y')—(R³¹)$_a$—X'—R³²—R³³ wherein R³⁰ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

Z' is alkanediyl, or substituted alkanediyl;

Y' is S;

R³¹ is alkanediyl or substituted alkanediyl;

x' is —C(=O)—;

R³² is a moiety that includes at least one divalent amino radical;

R³³ is a phenyl substituted with at least one halogen or cyano;

a is 0 or 1; and b is 0 or 1.

12. The compound of clause 11, wherein R³⁰ is selected from isoxazolyl, substituted isoxazolyl, oxazolyl, substituted oxazolyl, cyclohexyl, substituted cyclohexyl, piperidinyl, substituted piperidinyl, oxacyclopentyl, substituted oxacyclopentyl, oxacyclohexanyl, substituted oxacyclopentyl, thiophenyl, substituted thiophenyl, phenyl, substituted phenyl, pyridinyl, substituted pyridinyl, indolyl, substituted indolyl, furanyl, substituted furanyl, imidazolyl, or substituted imidazolyl.

13. The compound of clause 11, wherein R³⁰ is substituted isoxazolyl.

14. The compound of any one of clauses 11 to 13, wherein Z' is —CH₂—.

15. The compound of any one of clauses 11 to 14, wherein R³¹ is selected from $C_1$-$C_3$ alkanediyl or substituted $C_1$-$C_3$ alkanediyl.

16. The compound of any one of clauses 11 to 15, wherein R³² is selected from:

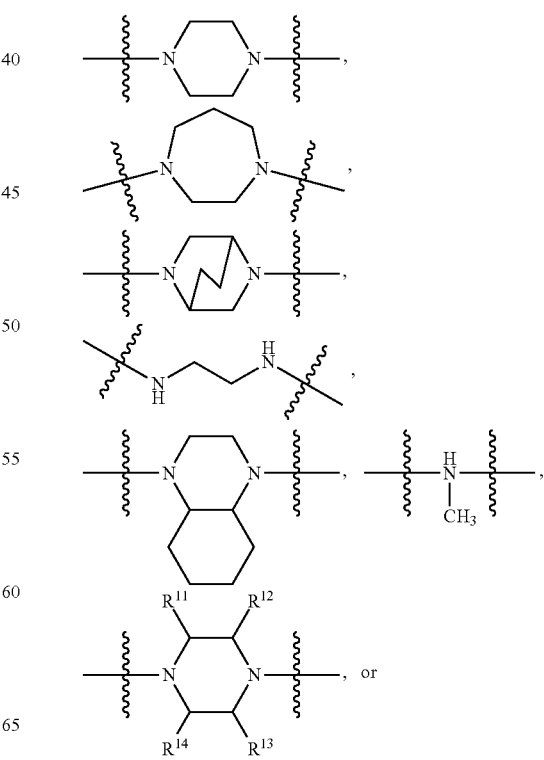

-continued

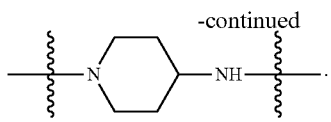

17. The compound of any one of clauses 11 to 16, wherein $R^{33}$ is a substituted phenyl having a structure of:

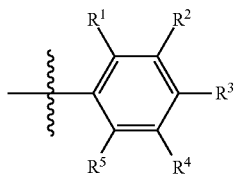

wherein each of $R^1$-$R^5$ is individually H, alkyl, halogen, or cyano, provided that at least one of $R^1$-$R^5$ is halogen or cyano.

18. The compound of clause 17, wherein $R^1$ is alkyl, halogen or cyano.

19. The compound of clause 11, wherein $R^{30}$ is substituted isoxazolyl, b is 1; a is 1; $R^{21}$ is —CH$_2$—; and $R^{32}$ is:

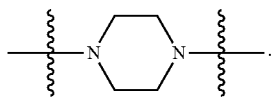

20. A pharmaceutical composition comprising at least one pharmaceutically acceptable additive, and a compound of any one of clauses 1 to 19.
21. A method for treating prostate cancer in a subject, comprising administering to the subject a therapeutically effective amount of a compound of any one of clauses 1 to 19.
22. The method of clause 21, wherein the prostate cancer is castration-resistant prostate cancer.
23. The method of clause 21 or 22, wherein the compound is orally administered.
24. The method of any one of clauses 21 to 23, wherein the method is used in combination with androgen deprivation therapy.
25. The method of any one of clauses 21 to 24, wherein the agent is co-administered with abiratrone.
26. The method of any one of clauses 21 to 25, wherein the method further comprises identifying a subject that is in need of treatment with the agent.

Illustrative compounds are shown in FIG. 1.

Figure 3:
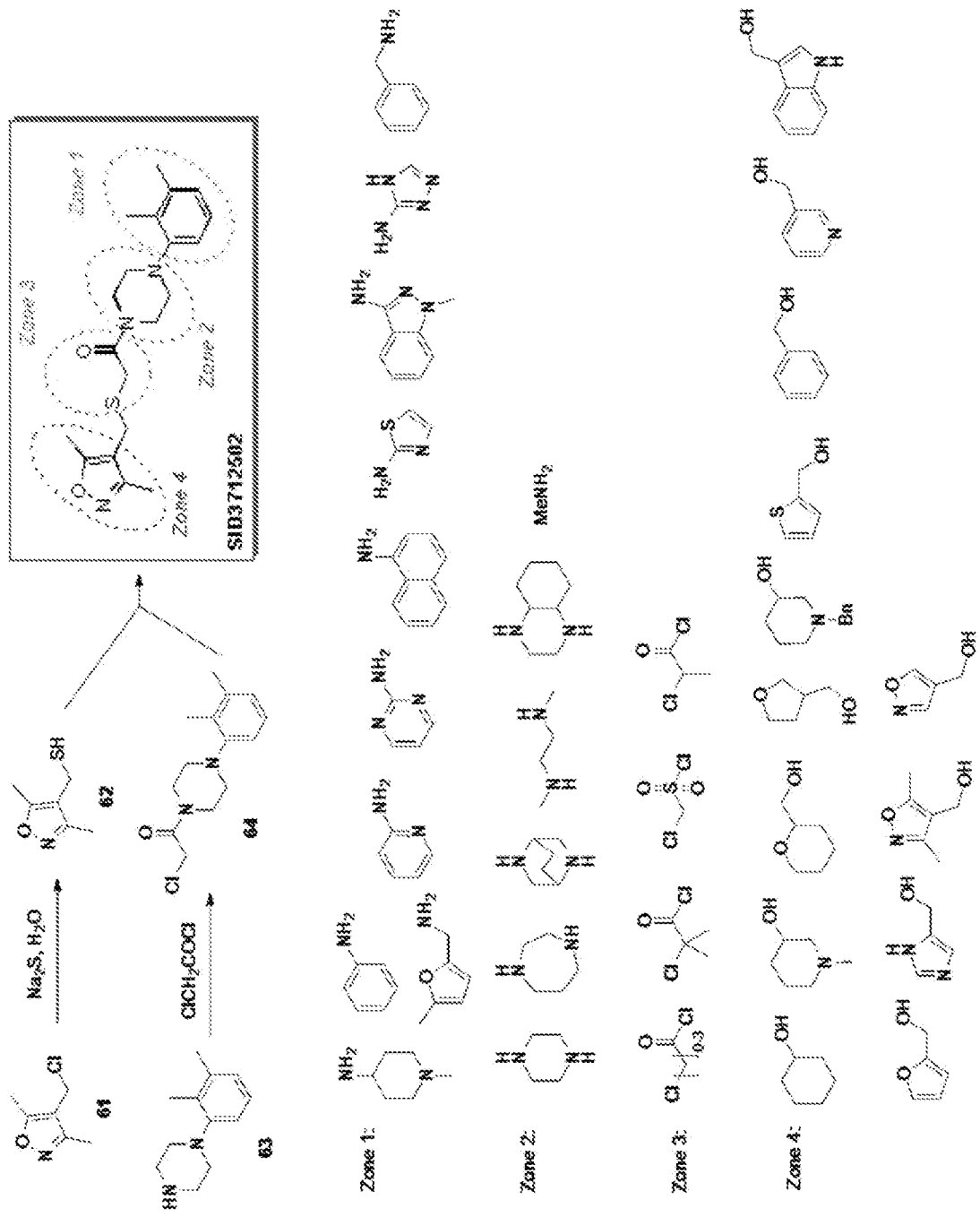
FIG. 3 is a reaction scheme.

An illustrative scheme 1 for making the compounds of formula I is shown in FIG. 3. Scheme 1 shows a synthesis of the parent structure that is amenable to the modifications lined out in a zone model. Isoxazole 61 can be obtained from the chloromethylation of 3,5-dimethylisoxazole, or via the corresponding alcohol, and will be converted to thiol 62. In situ alkylation of 62 with chloride 64 under the basic conditions of thiol formation leads to SID3712502. There are many methods known for pyridazine synthesis, and the preparation of 63 will follow one of these methods, most likely starting with the aniline. Acylation of 63 with chloroacetyl chloride provides 64. The building blocs shown in Scheme 1 for zones 1 and 4 have been selected to cover a large range of chemical diversity; in addition, they are commercially available and are therefore readily funneled into the segment-based synthesis plan. Zone 2 contains a few diamines that preserve the distance between zone 1 and zone 3, i.e. where the nitrogens are appropriately spaced, but this zone will also be contracted to a simple nitrogen linker in order to probe the need to maintain the overall distance and orientation between zone 1 and zone 4. Zone 3 contains another spacer functionality, but the amide carbonyl group might also be involved in specific interactions with the binding site on the protein. Therefore, the distance between the carboxyl function and the halide electrophile will be varied, and the carbonyl group will also be replaced by a sulfonyl function.

Synthesis of several of the compounds is described in detail below:

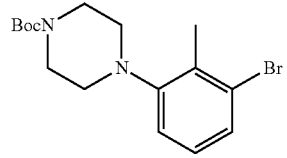 [SMILES: Cc1c(Br)cccc1N1CCN(C(=O)OC(C)(C)C)CC1]

tert-Butyl 4-(3-bromo-2-methylphenyl)piperazine-1-carboxylate (BRE454-64)

A microwave vial under Ar was charged with tert-butyl 1-piperazinecarboxylate (154 mg, 0.825 mmol), NaO-t-Bu (95.2 mg, 0.990 mmol), (rac)-BINAP (39.3 mg, 0.0619 mmol, 7.5% mol), Pd$_2$(dba)$_3$ (19.2 mg, 0.0206 mmol, 2.5% mol in Pd), and degassed toluene (2.1 mL). 2-Bromo-6-iodotoluene (121 µL, 0.825 mmol) was then added, and the mixture was heated in sealed vial at 80° C. for 19 h, cooled to rt, diluted with CH$_2$Cl$_2$, filtered over Celite, and concentrated. The mixture was purified by chromatography on SiO$_2$ (10% EtOAc/hexanes) to afford the product as a yellow oil (95 mg, 0.27 mmol, 32%): $^1$H NMR (500 MHz, CDCl$_3$) δ 7.30 (d, J=8.0 Hz, 1H), 7.02 (t, J=8.0 Hz, 1H), 6.95 (d, J=7.5 Hz, 1H), 3.57 (m, 4H), 2.83 (t, J=4.5 Hz, 4H), 2.40 (s, 3H), 1.49 (s, 9H).

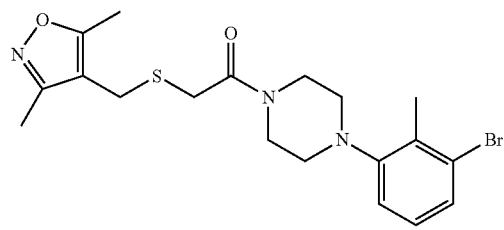 [SMILES: Cc1noc(C)c1CSCC(=O)N1CCN(c2cccc(Br)c2C)CC1]

1-(4-(3-Bromo-2-methylphenyl)piperazin-1-yl)-2-(((3,5-dimethylisoxazol-4-yl)methyl)thio) ethan-1-one (BRE454-75)

A solution of BRE454-64 (77.0 mg, 0.22 mmol) in THF (0.3 mL) at 0° C. was treated with 4 N HCl in dioxanes (1.3 mL) and stirred at 0° C. for 2 h. The yellow solid was collected by filtration, washed with Et$_2$O, dried (Na$_2$SO$_4$) and carried on to the next step without further purification.

To a solution of ([(3,5-dimethylisoxazol-4-yl)methyl] thio)acetic acid (35.0 mg, 0.174 mmol) in CH$_2$Cl$_2$ (1.7 mL) was added 4-(3-bromo-2-methylphenyl)piperazine HCl salt and triethylamine (121 µL, 0.870 mmol). The mixture was cooled to 0° C. and T3P (50% solution in EtOAc, 184 μL, 0.261 mmol) was added. The reaction mixture was allowed to warm to rt, stirred for 20 h, diluted with CH$_2$Cl$_2$, and washed with sat. NH$_4$Cl, sat. NaHCO$_3$, and brine. The organic portion was dried (Na$_2$SO$_4$), filtered, and concentrated to give a brown oil. The crude material was purified by chromatography on SiO$_2$ (60% EtOAc/hexanes, base washed with 0.1% NEt$_3$ prior to use) to give the product as a colorless oil (76.2 mg, 0.174 mmol, quant. 100% pure by ELSD): IR (ATR) 2921, 2820, 1637, 1587, 1562, 1460, 1428, 1282, 1237, 1195, 1136, 1038, 994, 913, 780, 731, 714 cm$^{-1}$; $^1$H NMR (400 MHz, CDCl$_3$) δ 7.32 (dd, J=0.8, 7.6 Hz, 1H), 7.03 (t, J=8.0 Hz, 1H), 6.94 (dd, J=0.8, 8.0 Hz, 1H), 3.77 (br s, 2H), 3.63 (s, 2H), 3.63-3.57 (m, 2H), 3.23 (s, 2H), 2.90 (t, J=4.4 Hz, 2H), 2.88-2.83 (m, 2H), 2.43 (s, 3H), 2.40 (s, 3H), 2.31 (s, 3H); $^{13}$C-NMR (125 MHz, CDCl$_3$) δ 167.6, 166.8, 159.7, 152.2, 132.9, 128.1, 127.4, 126.6, 118.3, 109.7, 52.1, 51.8, 46.8, 42.2, 32.1, 23.8, 18.2, 11.1, 10.2; HRMS (ESI) m/z calcd for C$_{19}$H$_{25}$N$_3$O$_2$BrS (M+H) 438.0845. found 438.0831.

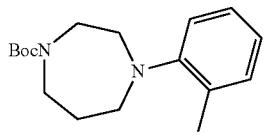 [SMILES: Cc1ccccc1N1CCCN(C(=O)OC(C)(C)C)CC1]

tert-Butyl 4-(o-tolyl)-1,4-diazepane-1-carboxylate (BRE454-66)

A microwave vial under Ar was charged with 1-Boc-homopiperazine (223 mg, 1.10 mmol), NaO-t-Bu (116 mg, 1.20 mmol), (rac)-BINAP (47.8 mg, 0.0752 mmol, 7.5% mol), Pd$_2$(dba)$_3$ (23.3 mg, 0.0251 mmol, 2.5% mol in Pd), and degassed toluene (2.8 mL). 2-Bromotoluene (175 mg, 1.00 mmol) was added, and the mixture was heated in a sealed vial at 80° C. for 19 h, cooled to rt, diluted with CH$_2$Cl$_2$, filtered over Celite, and concentrated. The crude material was purified by chromatography on SiO$_2$ (10% EtOAc/hexanes) to give the product as a yellow oil (139 mg, 0.479 mmol, 48%): IR (ATR) 2973, 2828, 1689, 1598, 1491, 1457, 1411, 1364, 1233, 1215, 1156, 1122, 878, 761, 725 cm$^{-1}$; $^1$H NMR (500 MHz, CDCl$_3$, rt, rotamers) δ 7.16 (d, J=6.0 Hz, 1H), 7.12 (d, J=6.0 Hz, 1H), 7.04 (d, J=7.5 Hz, 1H), 6.95 (t, J=7.0 Hz, 1H), 3.62-3.52 (m, 4H), 3.12-3.04 (m, 4H), 2.31 (s, 3H), 2.00-1.88 (m, 2H), 1.49 (s, 9H); $^{13}$C-NMR (100 MHz, CDCl$_3$, rt, rotamers) δ 155.6, 155.5, 153.9, 153.8, 132.9, 130.9, 126.5, 123.1, 120.8 (2C), 79.3, 56.2, 56.0, 55.5, 55.2, 48.4, 48.0, 46.2, 45.4, 29.0, 28.9, 28.5, 18.5; HRMS (ESI) m/z calcd for C$_{17}$H$_{27}$N$_2$O$_2$ (M+H) 291.2067. found 291.2062.

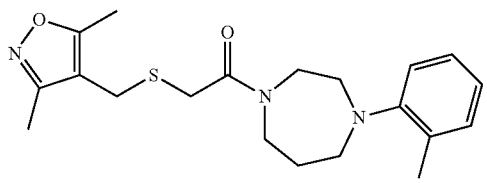 [SMILES: Cc1ccccc1N1CCCN(C(=O)CSCc2c(C)noc2C)CC1]

2-(((3,5-Dimethylisoxazol-4-yl)methyl)thio)-1-(4-(o-tolyl)-1,4-diazepan-1-yl)ethan-1-one (BRE454-76)

A solution of BRE454-66 (75.0 mg, 0.258 mmol) in THF (0.3 mL) at 0° C., was treated with 4 N HCl in dioxanes (1.6 mL), stirred at 0° C. for 2 h, and concentrated. The yellow solid was precipitated in Et$_2$O, collected by filtration, washed with Et$_2$O, dried (Na$_2$SO$_4$), and carried on to the next step without further purification.

To a solution of ([(3,5-dimethylisoxazol-4-yl)methyl]thio)acetic acid (46.0 mg, 0.229 mmol) in CH$_2$Cl$_2$ (2.3 mL) was added 4-(o-tolyl)-1,4-diazepane HCl salt and triethylamine (159 μL, 1.14 mmol). The mixture was cooled to 0° C. and T3P (50% solution in EtOAc, 242 μL, 0.343 mmol) was added. The reaction mixture was allowed to warm to rt, stirred for 20 h, diluted with CH$_2$Cl$_2$, and washed with sat. NH$_4$Cl, sat. NaHCO$_3$, and brine. The organic portion was dried (Na$_2$SO$_4$), filtered, and concentrated to give a brown oil. The crude material was purified by chromatography on SiO$_2$ (60% EtOAc/hexanes, base washed with 0.1% NEt$_3$ prior to use) to give BRE454-76 as a clear colorless oil (85.4 mg, 0.229 mmol, quant, 100% pure by ELSD): IR (ATR) 2945, 2825, 1634, 1598, 1491, 1447, 1423, 1215, 1194, 1136, 915, 762, 726 cm$^{-1}$; $^1$H NMR (400 MHz, CDCl$_3$, rt, rotamers) δ 7.20 (app. d, J=7.6 Hz, 1H), 7.17 (app. t, J=7.6 Hz, 1H), 7.05 (app. d, J=7.6 Hz, 1H), 7.01 (app. td, J=2.0, 7.2 Hz, 1H), 3.82-3.78 (m, 2H), 3.71-3.65 (m, 4H), 3.24-3.20 (m, 3H), 3.15 (t, J=5.2 Hz, 1H), 3.12-3.07 (m, 2H), 2.46 (app s, 3H), 2.32 (2×s, 6H), 2.04 (sept, J=6.0 Hz, 2H); $^{13}$C NMR (125 MHz, CDCl$_3$, rt, rotamers) δ 168.9, 168.8, 166.9, 166.8, 159.8 (2C), 153.4, 153.3, 132.9 (2C), 131.1 (2C), 126.7, 126.6, 123.6, 123.4, 120.8, 120.7, 109.9, 56.4, 55.8, 55.5, 54.9, 50.1, 47.6, 47.2, 44.9, 32.2, 32.0, 29.5, 28.2, 23.7, 18.5 (2C), 11.1, 10.2 (2C); HRMS (ESI) m/z calcd for C$_{20}$H$_{28}$N$_3$O$_2$S (M+H) 374.1897. found 374.1883.

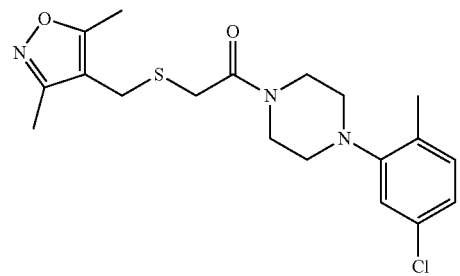 [SMILES: Cc1ccc(Cl)cc1N1CCN(C(=O)CSCc2c(C)noc2C)CC1]

1-(4-(5-Chloro-2-methylphenyl)piperazin-1-yl)-2-(((3,5-dimethylisoxazol-4-yl)methyl)thio) ethan-1-one (BRE454-58)

To a solution of ([(3,5-dimethylisoxazol-4-yl)methyl]thio)acetic acid (45.0 mg, 0.224 mmol) in CH$_2$Cl$_2$ (2.2 mL) was added 1-(5-chloro-2-methylphenyl)piperazine (56.5 mg, 0.268 mmol) and triethylamine (93.2 μL, 0.671 mmol). The mixture was cooled to 0° C., treated with T3P (50% solution in EtOAc, 237 μL, 0.335 mmol), warmed to rt, stirred for 20 h, diluted with CH$_2$Cl$_2$, and washed with sat. NH$_4$Cl, sat. NaHCO$_3$, and brine. The organic portion was dried (Na$_2$SO$_4$), filtered, and concentrated to give a brown oil. The crude material was purified by chromatography on SiO$_2$ (50% EtOAc/hexanes, base washed with 0.1% NEt$_3$ prior to use) to give the product as a clear colorless oil (88.1 mg, 0.224 mmol, quant, 99.9% pure by ELSD): IR (ATR) 2921, 2818, 1635, 1592, 1489, 1438, 1270, 1224, 1195, 1148, 1039, 924, 910, 818, 728 cm$^{-1}$; $^1$H NMR (400 MHz, CDCl$_3$) δ 7.11 (d, J=8.0 Hz, 1H), 6.99 (dd, J=2.0, 8.0 Hz, 1H), 6.94 (d, J=2.4 Hz, 1H), 3.76 (t, J=4.4 Hz, 2H), 3.63 (s, 2H), 3.59 (t, J=4.8 Hz, 2H), 3.23 (s, 2H), 2.91 (t, J=4.8 Hz, 2H), 2.86 (t, J=4.8 Hz, 2H), 2.43 (s, 3H), 2.30 (s, 3H), 2.27 (s, 3H); $^{13}$C NMR (125 MHz, CDCl$_3$) δ 167.6, 166.8, 159.7, 151.7, 132.1, 131.8, 130.9, 123.7, 119.7, 109.7, 51.6, 51.5, 46.8, 42.2, 32.0, 23.7, 17.4, 11.1, 10.2; HRMS (ESI) m/z calcd for C$_{19}$H$_{25}$N$_3$O$_2$ClS (M+H) 394.1351. found 394.1340.

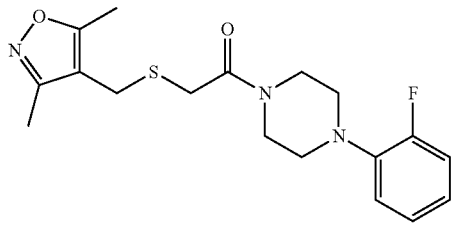 [SMILES: Cc1noc(C)c1CSCC(=O)N1CCN(c2ccccc2F)CC1]

2-(((3,5-Dimethylisoxazol-4-yl)methyl)thio)-1-(4-(2-fluorophenyl)piperazin-1-yl)ethan-1-one (BRE454-54)

To a solution of ([(3,5-dimethylisoxazol-4-yl)methyl]thio)acetic acid (75.8 mg, 0.377 mmol) in CH$_2$Cl$_2$ (3.8 mL) was added 1-(2-fluorophenyl)-piperazine (81.4 mg, 0.452 mmol) and triethylamine (262 μL, 1.88 mmol). The mixture was cooled to 0° C., treated with T3P (50% solution in EtOAc, 399 μL, 0.565 mmol), warmed to rt, stirred for 20 h, diluted with CH$_2$Cl$_2$, and washed with sat. NH$_4$Cl, sat. NaHCO$_3$, and brine. The organic portion was dried (Na$_2$SO$_4$), filtered, and concentrated to give a light brown oil. The crude material was purified by chromatography on SiO$_2$ (60% EtOAc/hexanes, base washed with 0.1% NEt$_3$ prior to use) to give the product as a slight yellow oil (134 mg, 0.369 mmol, 98%, 100% pure by ELSD): IR (ATR) 2918, 2827, 1636, 1613, 1500, 1439, 1237, 1195, 1147, 1031, 909, 811, 753, 725 cm$^{-1}$; $^1$H NMR (400 MHz, CDCl$_3$) δ 7.10-6.90 (m, 4H), 3.79 (t, J=5.2 Hz, 2H), 3.63-3.59 (m, 4H), 3.23 (s, 2H), 3.10 (t, J=4.8 Hz, 2H), 3.05 (t, J=5.2 Hz, 2H), 2.28 (s, 3H), 2.42 (s, 3H); $^{13}$C NMR (125 MHz, CDCl$_3$) δ 167.5, 166.8, 159.7, 155.7 (d, J$_{C-F}$=245.0 Hz), 139.4 (d, J$_{C-F}$=8.8 Hz), 124.5 (d, J$_{C-F}$=3.8 Hz), 123.3 (d, J$_{C-F}$=8.8 Hz), 119.2 (d, J$_{C-F}$=2.5 Hz), 116.3 (d, J=20.0 Hz), 109.7, 50.7 (d, J$_{C-F}$=2.5 Hz), 50.3 (d, J$_{C-F}$=2.5 Hz), 46.6, 41.9, 32.1, 23.7, 11.1, 10.2; HRMS (ESI) m/z calcd for C$_{18}$H$_{23}$N$_3$O$_2$FS (M+H) 364.1490. found 364.1474.

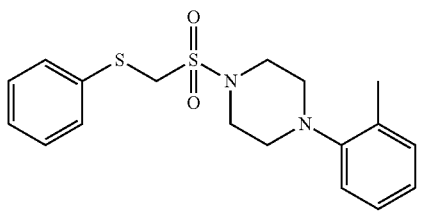 [SMILES: Cc1ccccc1N1CCN(S(=O)(=O)CSc2ccccc2)CC1]

1-(((Phenylthio)methyl)sulfonyl)-4-(o-tolyl)piperazine (BRE454-84)

A solution of 1-(2-methylphenyl)piperazine (0.500 g, 2.75 mmol) and triethylamine (0.390 mL, 2.75 mmol) in CH$_2$Cl$_2$ (9.8 mL) at 0° C. was treated with chloromethanesulfonyl chloride (0.460 g, 3.03 mmol), gradually warmed to rt, and stirred for 14 h. The reaction mixture was quenched with sat. NH$_4$Cl (3 mL) and extracted with EtOAc (3×20 mL). The combined organic portion was washed with water (2×10 mL) and brine (10 mL), dried (Na$_2$SO$_4$), filtered, and concentrated. The crude solid was filtered through a plug of SiO$_2$ (pretreated with 0.1% NEt$_3$ in 30% EtOAc/hexanes) and washed thoroughly with 30% EtOAc/hexanes to give the product as an orange solid (676 mg, 2.34 mmol, 85%): $^1$H NMR (400 MHz, CDCl$_3$) δ 7.21-7.17 (m, 2H), 7.05-7.00 (m, 2H), 4.57 (s, 2H), 3.63 (t, J=4.8 Hz, 4H), 2.98 (t, J=5.2 Hz, 4H), 2.31 (s, 3H).

A solution of this product (40.0 mg, 0.139 mmol), thiophenol (61.0 mg, 0.554 mmol), and Cs$_2$CO$_3$ (90.3 mg, 0.277 mmol) in DMF (0.28 mL) was stirred at 80° C. for 2 d. The crude reaction mixture was diluted with brine (10 mL) and extracted with EtOAc (20 mL). The organic portion was washed with brine (2×10 mL), dried (Na$_2$SO$_4$), and concentrated. The crude material was purified by chromatography on SiO$_2$ (20% EtOAc/hexanes) the product as a clear colorless oil (25.7 mg, 0.0709 mmol, 51%): IR (ATR) 3054, 2918, 2823, 1598, 1581, 1493, 1440, 1342, 1324, 1262, 1225, 1153, 1112, 1070, 954, 765, 744, 725, 691 cm$^{-1}$; $^1$H NMR (500 MHz, CDCl$_3$) δ 7.59 (d, J=7.5 Hz, 2H), 7.39-7.30 (m, 3H), 7.21-7.14 (m, 2H), 7.02 (t, J=7.5 Hz, 1H), 6.98 (d, J=8.0 Hz, 1H), 4.33 (s, 2H), 3.51 (t, J=4.5 Hz, 4H), 2.92 (t, J=4.5 Hz, 4H), 2.28 (s, 3H); $^{13}$C NMR (100 MHz, CDCl$_3$) δ 150.7, 133.4, 132.7, 131.2, 131.1, 129.4, 128.1, 126.7, 123.9, 119.4, 54.2, 51.8, 46.8, 17.7; HRMS (+ESI) m/z calcd for C$_{18}$H$_{23}$N$_2$O$_2$S$_2$ (M+H) 363.1195. found 363.1190.

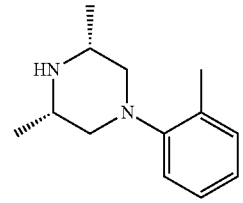

(3S,5R)-3,5-Dimethyl-1-(o-tolyl)piperazine (MK415-55)

A Schlenk flask backfilled with N$_2$ was charged with cis-2,6-dimethylpiperazine (0.11 g, 0.96 mmol), NaO-t-Bu (0.17 g, 1.8 mmol, (rac)-BINAP (8 mg, 0.01 mmol), Pd$_2$(dba)$_3$ (8 mg, 0.009 mmol), and degassed toluene (4 mL). The 2-bromotoluene (0.15 g, 0.88 mmol) was then added, and the mixture was heated under N$_2$ at 110° C. for 24 h, cooled to rt, diluted with CH$_2$Cl$_2$, filtered over Celite, and concentrated. The crude mixture was purified by chromatography on SiO$_2$ (CH$_2$Cl$_2$/MeOH 95:5) to give the product as clear, yellow oil (140 mg, 78%): $^1$H NMR (500 MHz, CDCl$_3$) δ 7.19-7.15 (m, 2H), 7.02-6.98 (m, 2H), 3.13-3.10 (m, 2H), 3.01 (d, J=10.5 Hz, 2H), 2.35-2.31 (m, 5H), 1.12 (d, J=6.5 Hz, 6H).

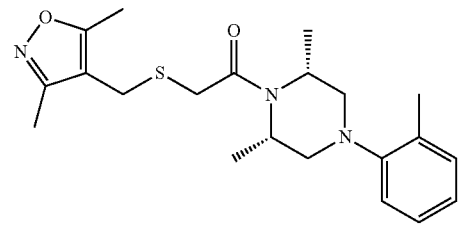 [SMILES: Cc1ccccc1N1C[C@@H](C)N(C(=O)CSCc2c(C)noc2C)[C@@H](C)C1]

1-((2S,6R)-2,6-Dimethyl-4-(o-tolyl)piperazin-1-yl)-2-(((3,5-dimethylisoxazol-4-yl)methyl)thio)ethanone (MK415-59)

To ([(3,5-dimethylisoxazol-4-yl)methyl]thio)acetic acid (30 mg, 0.14 mmol) in $CH_2Cl_2$ (2 mL) was added (3R,5S)-3,5-dimethyl-1-(o-tolyl)piperazine (35 mg, 0.17 mmol) and triethylamine (59 mL, 0.42 mmol). The mixture was cooled to 0° C. and T3P (50% sol'n in EtOAc, 150 mL, 0.21 mmol) was added. The reaction was allowed to warm to rt, stirred for 20 h, diluted with $CH_2Cl_2$, and washed with sat. $NH_4Cl$, sat. $NaHCO_3$, and brine. The organic portion was dried ($Na_2SO_4$), filtered, and concentrated. The crude material was purified by chromatography on $SiO_2$ (95:5 $CH_2Cl_2$/MeOH) to give the product as a light yellow oil (45 mg, 82%): $R_f$=0.5 (94:6 $CH_2Cl_2$/MeOH); HRMS (ESI) m/z calcd for $C_{21}H_{30}N_3O_2S$ ([M+H]$^+$) 388.2059. found 388.2053; $^1$H NMR (500 MHz, CDCl$_3$) δ 7.22-7.19 (m, 2H), 7.06-7.02 (m, 2H), 4.68 (brs, 1H), 4.05 (brs, 1H), 3.73-3.70 (m, 1H), 3.66-3.61 (m, 1H), 3.30-3.19 (m, 2H), 2.98-2.96 (m, 2H), 2.94-2.89 (m, 1H), 2.81-2.78 (m, 1H), 2.44 (s, 3H), 2.41 (s, 3H), 2.31 (s, 3H), 1.55 (rot, d, J=6.0 Hz, 3H), 1.48 (rot, d, J=6.0 Hz, 3H); $^{13}$C NMR (125 MHz, CDCl$_3$) δ 168.2, 166.7, 151.2, 133.3, 131.2, 126.8, 124.1, 119.6, 109.8, 57.0, 56.8, 49.8, 45.8, 32.0, 23.6, 21.6, 20.3, 18.2, 11.0, 10.1; IR (neat): 2975, 1629, 1491, 1422, 1327, 1127 cm$^{-1}$.

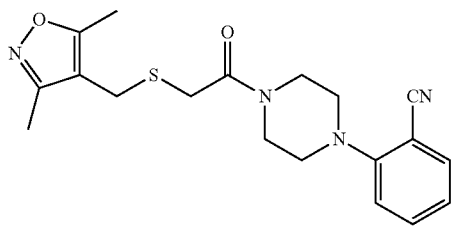 [SMILES: Cc1noc(C)c1CSCC(=O)N1CCN(c2ccccc2C#N)CC1]

2-(4-(2-(((3,5-Dimethylisoxazol-4-yl)methyl)thio)acetyl)piperazin-1-yl)benzonitrile (MK415-62)

To ([(3,5-dimethylisoxazol-4-yl)methyl]thio)acetic acid (18 mg, 0.085 mmol) in $CH_2Cl_2$ (1 mL) was added 2-(piperazin-1-yl)benzonitrile (16 mg, 0.085 mmol) and triethylamine (36 mL, 0.26 mmol). The mixture was cooled to 0° C. and T3P (50% sol'n in EtOAc, 91 mL, 0.13 mmol) was added. The reaction mixture was allowed to warm to rt, stirred for 20 h, diluted with $CH_2Cl_2$, and washed with sat. $NH_4Cl$, sat. $NaHCO_3$, and brine. The organic portion was dried ($Na_2SO_4$), filtered, and concentrated. The crude material was purified by chromatography on $SiO_2$ (95:5 $CH_2Cl_2$/MeOH) to give the product as a light yellow oil (9 mg, 29% yield): $R_f$ 0.43 (94:6 $CH_2Cl_2$/MeOH); HRMS (ESI) m/z calcd for $C_{19}H_{23}N_4O_2S$ ([M+H]$^+$) 371.1542. found 371.1536; $^1$H NMR (300 MHz, CDCl$_3$) δ 7.61 (dd, J=1.5, 7.8 Hz, 1H), 7.53 (dt, J=1.5, 8.4 Hz, 1H), 7.09 (t, J=7.5 Hz, 1H), 7.02 (d, J=8.4 Hz, 1H), 3.85 (t, J=4.8 Hz, 2H), 3.69 (t, J=4.8 Hz, 2H), 3.64 (s, 2H), 3.25 (app s, 2H), 3.23 (m, 2H) 3.17 (t, J=5.4 Hz, 2H), 2.44 (s, 3H), 2.30 (s, 3H); IR (neat): 2919, 2216, 1637, 1593, 1420, 1232 cm$^{-1}$.

In certain embodiments, the agents disclosed herein may have one or more of the following properties:

AR-GFP EC$_{50}$ (primary assay): ≤10 uM; concentration-dependent, appropriate curve.

Selective vs. other translocation targets; EC$_{50}$≥5 fold.

Chemical purity/integrity: >90% pure by LCMS/UV/ELS detection, structure consistent with other analytical data (NMR).

Mechanism of action: Mechanism is consistent with potency and characterization in cell based assays and does not involve kinase inhibition, DNA binding or unspecific/unknown cytotoxicity.

Cell Proliferation Assays in AR-positive cells: ≤5 uM; in AR-negative cells: >10 uM.

ADMET Predictions: Acceptable within Lipinski/Veber Rules, adequate solubility, permeability, low CYP and hERG channel inhibition, etc.

Half-life in the order of 4-6 h.

Limited metabolism (i.e. renal elimination).

Bioavailability greater than 30%.

Tumor penetration with concentrations maintained in the tumor at or above the EC$_{50}$'s obtained from cell culture.

Compounds 559, 562, 475, 476, 484, and 458 are all active in the PSA luciferase assay at sub-micromolar EC50s (450-900 nM), and they are inactive against androgen receptor (AR) negative cell lines in cell proliferation assays.

Additional compounds are shown below:

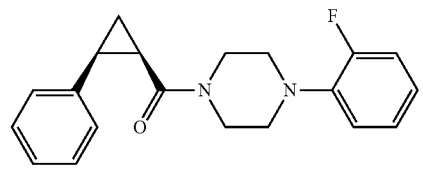

UPCMLD35AJKJ056582
Short #582
Sample weight: 0.88 mg
Chemical Formula: $C_{20}H_{21}FN_2O$
Exact Mass: 324.16

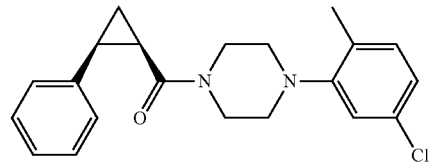

UPCMLD35AJKJ056583
Short #583
Sample weight: 0.55 mg
Chemical Formula: $C_{21}H_{23}ClN_2O$
Exact Mass: 354.15

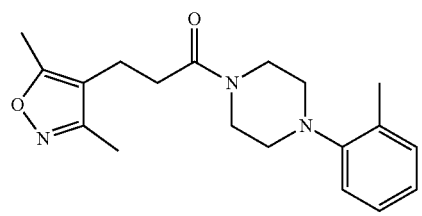

UPCMLD35AJKJ056588
Short #588
Sample weight: 0.70 mg
Chemical Formula: $C_{19}H_{25}N_3O_2$
Exact Mass: 327.19

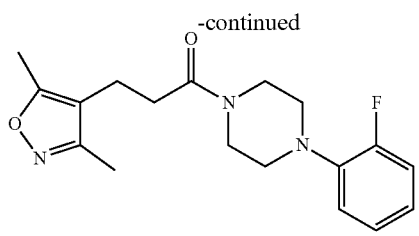

UPCMLD35AJKJ056589
Short #589
Sample weight: 0.54 mg
Chemical Formula: $C_{18}H_{22}FN_3O_2$
Exact Mass: 381.17

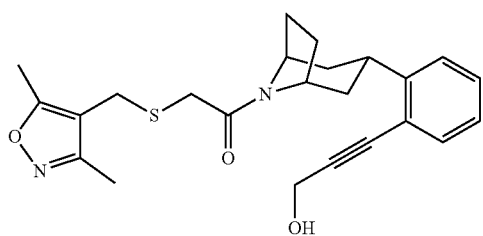

UPCMLD35AJKJ056571
Short #571
Sample weight: 0.54 mg
Chemical Formula: $C_{24}H_{28}N_2O_3S$
Exact Mass: 424.18

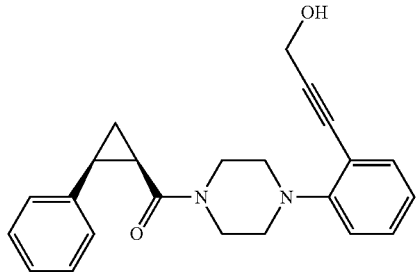

JKJ584-25
Short #: 425
Batch #: 1
Sample weight: 0.56 mg
Chemical Formula: $C_{23}H_{24}N_2O_2$
Exact Mass: 360.18

Figure 4A:
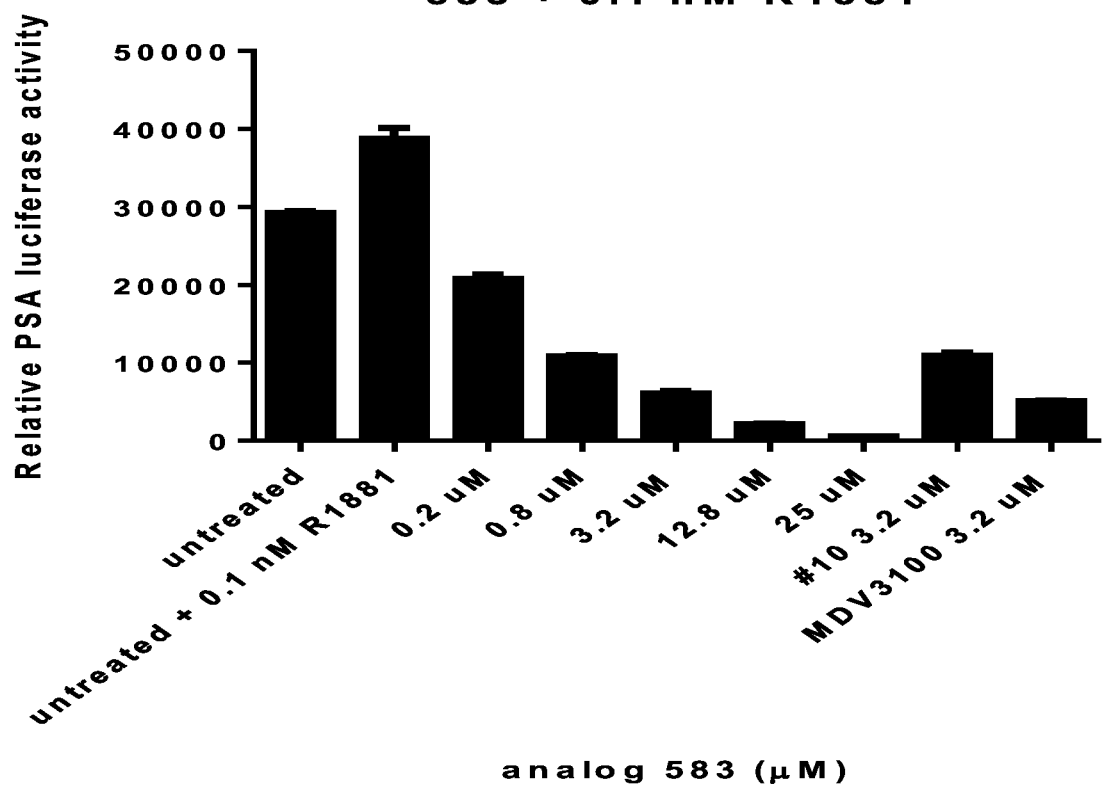
FIG. 4A is a graph showing the effect of compound #583 at indicated concentrations on PSA-driven luciferase activity in C4-2 cells.
Figure 4B:
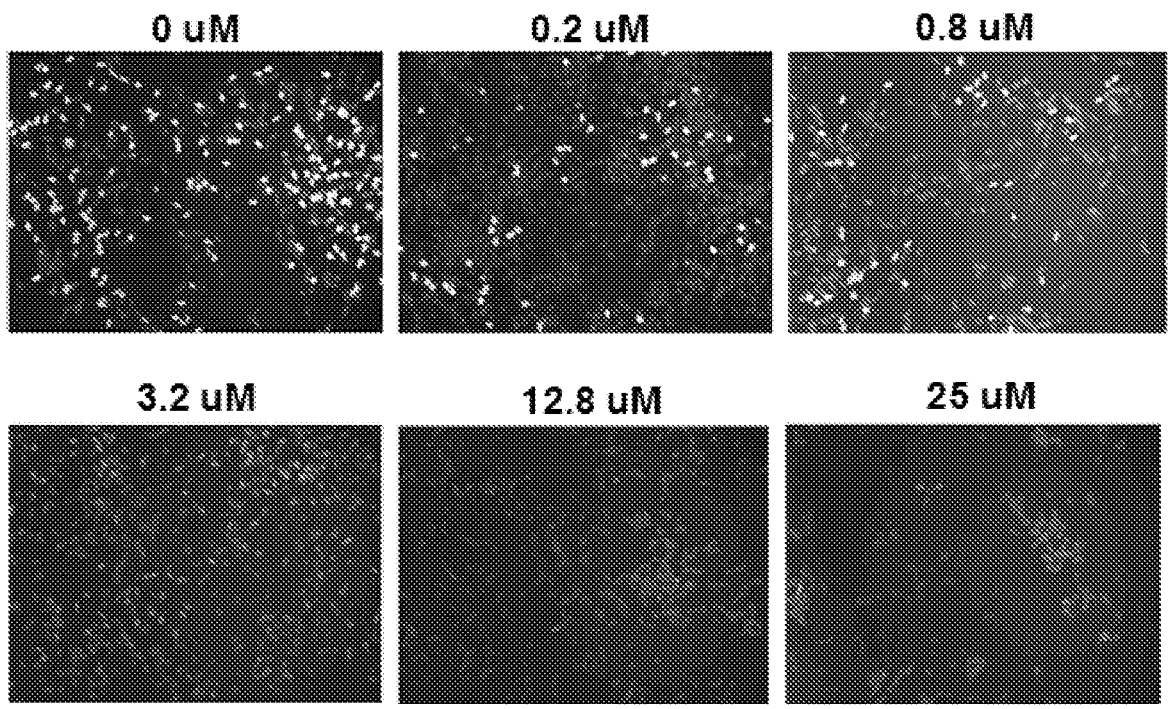
FIG. 4B shows the effect of compound #583 at indicated concentrations on C4-2 cell proliferation in BrdU assay.
Figure 4C:
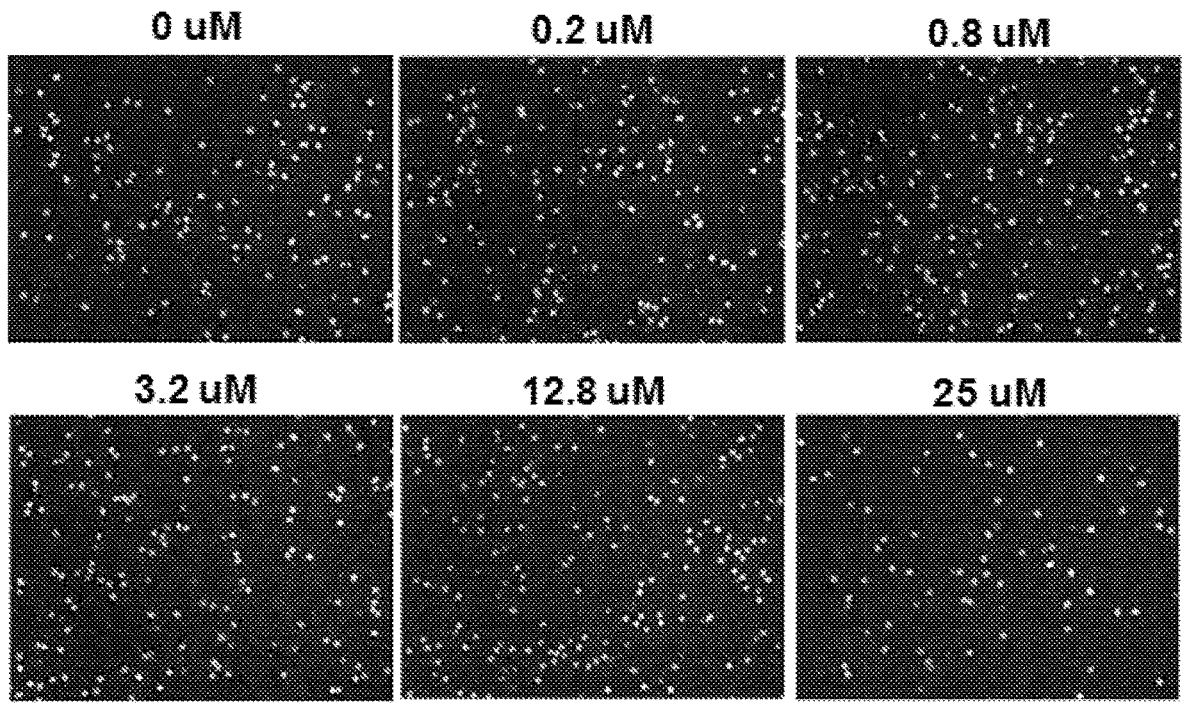
FIG. 4C shows the effect of analog #583 at indicated concentrations on PC3 cell proliferation in BrdU assay.

Compound #583 appears to be very potent, with an IC50>1 uM in inhibiting AR-dependent PSA promoter activity (FIG. 4A). As expected, #583 inhibited proliferation of AR-positive C4-2 (FIG. 4B), but not AR-negative PC3 (FIG. 4C), prostate cancer cells. Also, #583 does not contain a sulfur atom in the structure and should therefore be more resistant to oxidative metabolic degradation than the sulfur-containing compounds.

Figure 5:
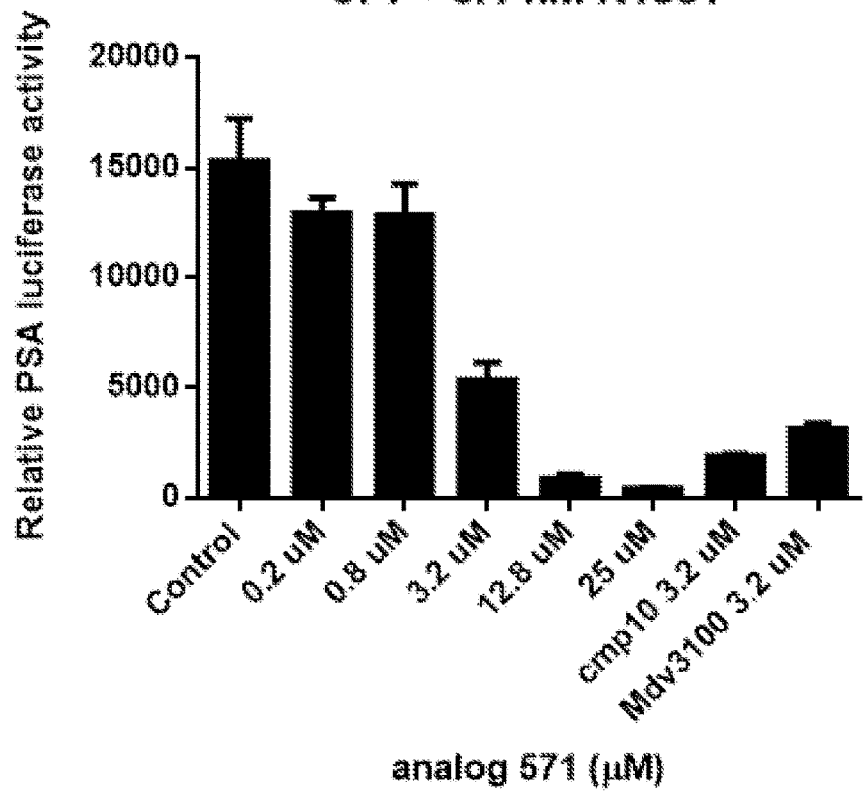
FIG. 5 is a graph showing the effect of compound #571 at indicated concentrations on PSA-driven luciferase activity in C4-2 cells.

Compounds #571 and #425 were developed for conjugation to agarose matrix. #571 is quite active, with an IC50 of ~3 uM in the inhibition of AR activation of PSA promoter in a luciferase assay (FIG. 5).

Pharmaceutical Compositions and Method of Use

The agents disclosed herein may be administered to a subject for treating prostate cancer, particularly castration-resistant prostate cancer. In certain embodiments a subject is identified as having castration-resistant prostate cancer that may be responsive to the agents disclosed herein. For example, patients that are offered any form of androgen deprivation therapy or anti-androgen therapy, including treatment with abiraterone or MDV3100, for the management of prostate cancer would be candidates for treatment with the agents disclosed herein.

Administration of the agent may reduce the nuclear level of androgen receptor in castration-resistant prostate cancer (CRPC) cells relative to the untreated control CRPC cells. Reducing nuclear androgen receptor levels is expected to inhibit its activation. Reduction of androgen receptor activation can be determined via measuring androgen-responsive genes, such as prostate-specific antigen (PSA).

In certain embodiments, the agent may be co-administered with another therapeutic agent such as, for example, an immunostimulant, an anti-cancer agent, an antibiotic, or a combination thereof. In particular, the agents targeting AR nuclear localization could be used in combination with standard androgen deprivation therapy (ADT) or with abiratrone in the treatment of CRPC.

The agents disclosed herein can be included in a pharmaceutical composition for administration to a subject. The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The agents disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agent can be for either prophylactic or therapeutic purpose. When provided prophylactically, the agent is provided in advance of any symptom. The prophylactic administration of the agents serves to prevent or ameliorate any subsequent disease process. When provided therapeutically, the compound is provided at (or shortly after) the onset of a symptom of disease or infection.

For prophylactic and therapeutic purposes, the agent can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

In view of the many possible embodiments to which the principles of the disclosed compounds, compositions and methods may be applied, it should be recognized that the illustrated embodiments are only preferred examples and should not be taken as limiting the scope of the invention.

What is claimed is:

1. A compound, or a pharmaceutically acceptable salt or ester thereof, having a formula I of:

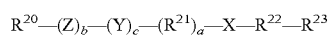

wherein $R^{20}$ is unsubstituted phenyl;
Z is alkanediyl or substituted alkanediyl;
Y is S;
$R^{21}$ is

X is —C(=O)— or —S(=O)(=O)—;
$R^{22}$ is

R²³ is a substituted phenyl having a structure of:

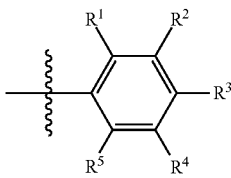

wherein each of R¹-R⁵ is individually H, alkyl, halogen, cyano, or substituted alkynyl, provided that R¹ is not H and R⁴ is halogen;
a is 1;
b is 0 or 1; and
c is 0 or 1;
provided that if X is —C(=O)— then Y is not S.

2. The compound of claim 1, wherein R⁴ is chloro.

3. The compound of claim 1, wherein b and c are each 0, and X is —C(=O)—.

4. The compound of claim 1, wherein X is —C(=O)—.

5. The compound of claim 1, wherein the compound is

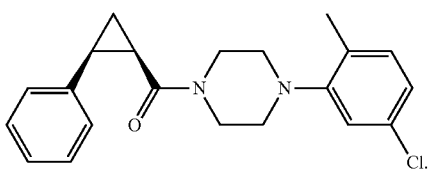 [SMILES: Cc1ccc(Cl)cc1N1CCN(C(=O)[C@@H]2C[C@@H]2c2ccccc2)CC1]

6. A pharmaceutical composition comprising at least one pharmaceutically acceptable additive and a compound of claim 1.

7. The pharmaceutical composition of claim 6, wherein the pharmaceutically acceptable additive is selected from physiological saline, balanced salt solution, aqueous dextrose, glycerol, mannitol, lactose, starch or magnesium stearate.

8. A compound, or a pharmaceutically acceptable salt or ester thereof, having a formula I of:

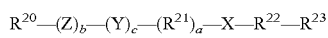

wherein R²⁰ is unsubstituted phenyl;
Z is alkanediyl or substituted alkanediyl;
Y is S;
R²¹ is

X is —C(=O)— or —S(=O)(=O)—;
R²² is

R²³ is a substituted phenyl having a structure of:

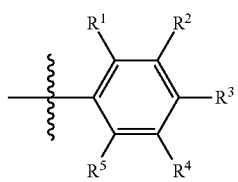

wherein each of R¹-R⁵ is individually H, alkyl, halogen, cyano, or substituted alkynyl, provided that R¹ is alkyl, halogen or cyano and R⁴ is halogen;
a is 1;
b is 0 or 1; and
c is 0 or 1;
provided that if X is —C(=O)— then Y is not S.

9. The compound of claim 8, wherein R¹ is methyl.

10. The compound of claim 8, wherein b and c are each 0, and X is —C(=O)—.

11. The compound of claim 8, wherein X is —C(=O)—.

12. A pharmaceutical composition comprising at least one pharmaceutically acceptable additive and a compound of claim 8.

13. The pharmaceutical composition of claim 12, wherein the pharmaceutically acceptable additive is selected from physiological saline, balanced salt solution, aqueous dextrose, glycerol, mannitol, lactose, starch or magnesium stearate.

14. A pharmaceutical composition comprising at least one pharmaceutically acceptable additive and a compound of claim 2.

15. The pharmaceutical composition of claim 14, wherein the pharmaceutically acceptable additive is selected from physiological saline, balanced salt solution, aqueous dextrose, glycerol, mannitol, lactose, starch or magnesium stearate.

* * * * *